US005169761A

United States Patent [19]

Benson et al.

[11] Patent Number: 5,169,761

[45] Date of Patent: Dec. 8, 1992

[54] DNA ENCODING AND EXPRESSION SYSTEMS FOR ALVEOLAR SURFACTANT PROTEINS

[75] Inventors: Bradley J. Benson, San Francisco; Robert T. White, Fremont; James W. Schilling, Jr., Palo Alto; Douglas I. Buckley, Woodside; Robert M. Scarborough, Belmont, all of Calif.

[73] Assignee: California Biotechnology Inc., Mountain View, Calif.

[21] Appl. No.: 699,960

[22] Filed: May 14, 1991

Related U.S. Application Data

[60] Division of Ser. No. 524,360, May 17, 1990, Pat. No. 5,104,853, which is a continuation-in-part of Ser. No. 266,443, Nov. 1, 1988, abandoned, which is a continuation-in-part of Ser. No. 117,099, Nov. 4, 1987, abandoned, which is a continuation-in-part of Ser. No. 8,453, Jan. 29, 1987, abandoned, which is a continuation-in-part of Ser. No. 857,715, May 30, 1986, Pat. No. 4,933,280, which is a continuation-in-part of Ser. No. 808,843, Dec. 13, 1985, Pat. No. 4,912,038, which is a continuation-in-part of Ser. No. 680,358, Dec. 11, 1984, Pat. No. 4,659,805.

[51] Int. Cl.[5] ........................ C12P 21/02; C12N 5/18; C12N 15/18; C12N 1/21

[52] U.S. Cl. .............................. 435/69.1; 435/252.33; 435/320.1; 435/240.2; 435/252.3; 536/27

[58] Field of Search ............... 435/252.33, 320.1, 69.1, 435/252.3, 240.2; 536/27

[56] References Cited

U.S. PATENT DOCUMENTS

| | | | |
|---|---|---|---|
| 4,312,860 | 1/1982 | Clements | 514/78 |
| 4,506,013 | 3/1985 | Heshberger et al. | 435/34 |
| 4,562,003 | 12/1985 | Lewicki | 436/520 |
| 4,659,805 | 4/1987 | Schilling, Jr. et al. | 530/350 |
| 4,853,332 | 8/1989 | Mark et al. | 435/252.33 |
| 4,912,038 | 3/1990 | Schilling, Jr. et al. | 435/69.1 |
| 5,013,720 | 5/1991 | Whitsett | 514/12 |

FOREIGN PATENT DOCUMENTS

WO87/06943 11/1987 PCT Int'l Appl. .

91/00871 1/1991 PCT Int'l Appl. .

OTHER PUBLICATIONS

Warr et al., *PNAS* vol. 84, Oct. 1087, 7915–7919.

Johansson et al., *FEBS Letters* vol. 232, May 1988, pp. 61–64.

Whitsett et al., *Pediatric Res.* (1986) 20(5):460–467.

Whitsett et al., *Pediatric Res.* (1986) 20(8):744–749.

Young et al., *Proc. Natl. Acad. Sci.* (1983) 80:1194–1198.

Yu et al., *Pediatric Res.* (1988) 23(1):23–30.

Kwong et al., *Pediatrics* (1985) 76(4):585–592.

Maki et al., *Nakoya Med. J.* (1982) 27:213–226.

Notter et al., *Chem. Phys. Lipids* (1987) 44(1):1–18.

Phizackerley et al., *Biochem. J.* (1979) 183:731–736.

Robertson, *Eur. J. Respir. Dis.* (1987) 71(Supplement 153):242–248.

Shelley et al., *Lung* (1982) 160:195–206.

Sueishi et al., *Biochem. Biophys. Acta* (1981) 665:442–453.

Takahashi et al., *Biochem. Biophys. Res. Commun.* (1986) 135(2):527–532.

Tanaka et al., *Chem. Pharm. Bull.* (1983) 31:4100–4109.

Weaver et al., *Biol. Abstracts* vol. 80, No. 7, abstract No. 63225.

Weaver et al., *Gen. Pharmacol.* (1988) 19(3):361–368.

White et al., *Nature* (1985) 317:361–363.

Whitsett et al., *Chem. Abstracts* vol. 102, abstract No. 217062f.

Fujiwara et al., *Lancet* (Jan. 1980) pp. 55–59.

Glasser et al., *J. Biol. Chem.* (1988) 263(1):9–12.

Hallman et al., *Pediatrics* (1983) 71(4):473–482.

(List continued on next page.)

*Primary Examiner*—Richard A. Schwartz
*Assistant Examiner*—James Ketter
*Attorney, Agent, or Firm*—Morrison & Foerster

[57] ABSTRACT

Various specific human SP-18 and human SP-5 derived peptides have alveolar surfactant protein (ASP) activity. These peptides are prepared using synthetic methods or by recombinant techniques.

4 Claims, 19 Drawing Sheets

Human SP5

```
                                            ATG GAT GTG GGC AGC AAA GAG GTC CTG ATG GAG AGC CCG CCG GAC TAC TCC GCA GCT
                                            MET Asp Val Gly Ser Lys Glu Val Leu MET Glu Ser Pro Pro Asp Tyr Ser Ala Ala
                                             1                                                                       19

                N Term
CCC CGG GGC CGA TTT GGC ATT CCC TGC TGC CCA GTG CAC CTG AAA CGC CTT CTT ATC GTG GTG GTG GTG GTG GTC CTC ATC GTC GTG GTG
Pro Arg Gly Arg Phe Gly Ile Pro Cys Cys Pro Val His Leu Lys Arg Leu Leu Ile Val Val Val Val Val Val Leu Ile Val Val Val
 20  21  22  23  24  25  26  27  28  29  30  31  32  33  34  35  36  37

                                    C Term
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
                     55  56  57  58  59  60                  65                  70              74
```

OTHER PUBLICATIONS

Hallman et al., *Pediatric Clinics of North America* (1982) 29(5):1057-1075.
Hallman et al., *J. Perinatal Med.* (1987) 15(5):463-468.
Helfman et al., *Proc. Natl. Acad. Sci.* (1983) 80:31-35.
Hewick et al., *J. Biol. Chem.* (1981) 256(15):7990-7997.
Hunkapiller et al., *Methods in Enzymol.* (1983) 91:399-413.
Jacobs et al., *J. Biol. Chem.* (1987) 262(20):9808-9811.
Katayal et al., *Chem. Abstracts* (1984) vol. 101, abstract No. 147230n.
Katayal et al., *Chem. Abstracts* (1981) vol. 95, abstract No. 199389y.
Katayal et al., *Biochem. Biophys. Acta* (1981) 670:323-331.
King et al., *Amer. J. Physiol.* (1973) 224(4):788-795.
Balis et al., *Lab. Invest.* (1985) 52(6):657-669.
Balis et al., *Exper. Lung Res.* (1984) 6:197-213.
Benson et al., *Proc. Natl. Acad. Sci.* (1985) 82:6379-6383.
Brandwein et al., *Proc. Natl. Acad. Sci.* (1981) 78(7):4241-4245.
Breslow et al., *Proc. Natl. Acad. Sci.* (1982) 79:6861-6865.
Bruni et al., *Biochem. Exp. Biol.* (1978) 14(3):209-214.
Chirgwin et al., *Biochem.* (1979) 18(4):5294-5299.
Claypool et al., *J. Clin. Invest.* (1984) 74:677-684.
Claypool et al., *Exper. Lung Res.* (1984) 6:215-222.
Dayhoff et al., *Atlas of Protein Sequence and Structure* (1972) 5:89-99.
Eistetter et al., *Anticancer Res.* (1987) 7(5A):909.
Enhorning et al., *Pediatrics* (1985) 76(2):145-153.
Floros et al., *J. Biol. Chem.* (1986) 261(19):9029-9033.

Human SP5 cDNA #18

```
GAATTCGGGGAG AGCATAGCAC CTGCAGCAAG ATG GAT GTG GGC AGC AAA GAG GTC CTG ATG GAG AGC CCG CCG GAC TAC TCC GCA GCT
                                   MET Asp Val Gly Ser Lys Glu Val Leu MET Glu Ser Pro Pro Asp Tyr Ser Ala Ala
                                    1
            100
CCC CGG GGC CGA TTT GGC ATT CCC TGC TGC CCA GTG CAC CTG AAA CGC CTT CTT ATC GTG GTG GTG GTG GTG GTC CTC ATC GTG GTG GTG
Pro Arg Gly Arg Phe Gly Ile Pro Cys Cys Pro Val His Leu Lys Arg Leu Leu Ile Val Val Val Val Val Val Leu Ile Val Val Val
                 24  25
                        200
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
                                                         65
                                    300
CAA CGC CTG GCC CTG AGT GAG CAC CTG GTT ACC ACT GCC ACC TTC TCC ATC GGC TCC ACT GGC CTC GTG GTG TAT GAC TAC CAG CAG CTG
Gln Arg Leu Ala Leu Ser Glu His Leu Val Thr Thr Ala Thr Phe Ser Ile Gly Ser Thr Gly Leu Val Val Tyr Asp Tyr Gln Gln Leu
 80                                                                                                               108
                                                400
CTG ATC GCC TAC AAG CCA GCC CCT GGC ACC TGC TGC TAC ATC ATG AAG ATA GCT CCA GAG AGC ATC CCC AGT CTT GAG GCT CTC AAT AGA
Leu Ile Ala Tyr Lys Pro Ala Pro Gly Thr Cys Cys Tyr Ile MET Lys Ile Ala Pro Glu Ser Ile Pro Ser Leu Glu Ala Leu Asn Arg
                                                                                                                  138
                                                            500
AAA GTC CAC AAC TTC CAG ATG GAA TGC TCT CTG CAG GCC AAG CCC GCA GTG CCT ACG TCT AAG CTG GGC CAG GCA GAG GGG CGA GAT GCA
Lys Val His Asn Phe Gln MET Glu Cys Ser Leu Gln Ala Lys Pro Ala Val Pro Thr Ser Lys Leu Gly Gln Ala Glu Gly Arg Asp Ala
                                                                            600
GGC TCA GCA CCC TCC GGA GGG GAC CCG GCC TTC CTG GGC ATG GCC GTG AAC ACC CTG TGT GGC GAG GTG CCG CTC TAC TAC ATC TAG GAC
Gly Ser Ala Pro Ser Gly Gly Asp Pro Ala Phe Leu Gly MET Ala Val Asn Thr Leu Cys Gly Glu Val Pro Leu Tyr Tyr Ile End
                                                            186                                     197
                                                                               700
G CCTCCGGTGA GCAGGGTCAG TGGAAGCCCC AACGGGAAAG GAAACGCCCC GGGCAAAGGG TCTTTTGCAG CTTTTGCAGA CGGGCAAGAA GCTGCTTCTG CCCACAC
                                                                                  800
CGC AGGGACAAAC CCTGGAGAAA TGGGAGCTTG GGGAGAGGAT GGGAGTGGGC AGAGGTGGCA CCCAGGGGCC CGGGAACTCC TGCCACAACA GAATAAAGCA GCCTG

ATTG AAAAAAAAAAAA
```

FIG. 1

Human SP5 cDNA #19

```
                   GAATTCGGAGCAC CTGCAGCAAG ATG GAT GTG GGC AGC AAA GAG GTC CTG ATG GAG AGC CCG CCG GAC TAC TCC GCA GCT
                                            MET Asp Val Gly Ser Lys Glu Val Leu MET Glu Ser Pro Pro Asp Tyr Ser Ala Ala
                                             1
                          100
CCC CGG GGC CGA TTT GGC ATT CCC TGC TGC CCA GTG CAC CTG AAA CGC CTT CTT ATC GTG GTG GTG GTG GTG GTC CTC ATC GTC GTG GTG
Pro Arg Gly Arg Phe Gly Ile Pro Cys Cys Pro Val His Leu Lys Arg Leu Leu Ile Val Val Val Val Val Val Leu Ile Val Val Val
                 24  25
                                     200
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
                                                             65
                                                 300
CAA CGC CTG GCC CTG AGT GAG CAC CTG GTT ACC ACT GCC ACC TTC TCC ATC GGC TCC ACT GGC CTC GTG GTG TAT GAC TAC CAG CAG CTG
Gln Arg Leu Ala Leu Ser Glu His Leu Val Thr Thr Ala Thr Phe Ser Ile Gly Ser Thr Gly Leu Val Val Tyr Asp Tyr Gln Gln Leu
 80                                                                                                              108
                                                             400
CTG ATC GCC TAC AAG CCA GCC CCT GGC ACC TGC TGC TAC ATC ATG AAG ATA GCT CCA GAG AGC ATC CCC AGT CTT GAG GCT CTC ACT AGA
Leu Ile Ala Tyr Lys Pro Ala Pro Gly Thr Cys Cys Tyr Ile MET Lys Ile Ala Pro Glu Ser Ile Pro Ser Leu Glu Ala Leu Thr Arg
                                                                                                                  138
                                                                             500
AAA GTC CAC AAC TTC CAG ATG GAA TGC TCT CTG CAG GCC AAG CCC GCA GTG CCT ACG TCT AAG CTG GGC CAG GCA GAG GGG CGA GAT GCA
Lys Val His Asn Phe Gln MET Glu Cys Ser Leu Gln Ala Lys Pro Ala Val Pro Thr Ser Lys Leu Gly Gln Ala Glu Gly Arg Asp Ala
                                                                                          600
GGC TCA GCA CCC TCC GGA GGG GAC CCG GCC TTC CTG GGC ATG GCC GTG AGC ACC CTG TGT GGC GAG GTG CCG CTC TAC TAC ATC TAG GAC
Gly Ser Ala Pro Ser Gly Gly Asp Pro Ala Phe Leu Gly MET Ala Val Ser Thr Leu Cys Gly Glu Val Pro Leu Tyr Tyr Ile End
                                                                186                                         197
                                                                                     700
GCCTCCGGTG AGCAGGGTCA GTGGAAGCCC CAACGGGAAA GGAAACGCCC CGGGCAAAGG GTCTTTTGCA GCTTTTGCAG ACGGGCAAGA AGCTGCTTCT GCCCACACC
                                                                                800
G CAGGGACAAG CCCTGGAGAA ATGGGAGCTT GGGGAGAGGA TGGGAGTGGG CAGAGGTGGC GCCCAGGGGC CCGGGAACTC CTGCCACAAC AGAATAAAGC AGCCTGA

TTG AAAAAAAAAAAA
```

FIG. 2

Human SP5

```
                                            ATG GAT GTG GGC AGC AAA GAG GTC CTG ATG GAG AGC CCG CCG GAC TAC TCC GCA GCT
                                            MET Asp Val Gly Ser Lys Glu Val Leu MET Glu Ser Pro Pro Asp Tyr Ser Ala Ala
                                             1                                                                      19

                N Term
CCC CGG GGC CGA TTT GGC ATT CCC TGC TGC CCA GTG CAC CTG AAA CGC CTT CTT ATC GTG GTG GTG GTG GTG GTC CTC ATC GTC GTG GTG
Pro Arg Gly Arg Phe Gly Ile Pro Cys Cys Pro Val His Leu Lys Arg Leu Leu Ile Val Val Val Val Val Val Leu Ile Val Val Val
 20  21  22  23  24  25  26  27  28  29  30  31  32  33  34  35  36  37

                                    C Term
ATT GTG GGA GCC CTG CTC ATG GGT CTC CAC ATG AGC CAG AAA CAC ACG GAG ATG GTT CTG GAG ATG AGC ATT GGG GCG CCG GAA GCC CAG
Ile Val Gly Ala Leu Leu MET Gly Leu His MET Ser Gln Lys His Thr Glu MET Val Leu Glu MET Ser Ile Gly Ala Pro Glu Ala Gln
                     55  56  57  58  59  60                  65                  70              74
```

FIG. 3

```
Human SP18 cDNA #3     GAATTCGGGTGCC ATG GCT GAG TCA CAC CTG CTG CAG TGG CTG CTG CTG CTG CTG CCC ACG
                                     MET Ala Glu Ser His Leu Leu Gln Trp Leu Leu Leu Leu Leu Pro Thr
                                      1
                                            100
CTC TGT GGC CCA GGC ACT GCT GCC TGG ACC ACC TCA TCC TTG GCC TGT GCC CAG GGC CCT GAG TTC TGG TGC CAA AGC CTG GAG CAA GCA
Leu Cys Gly Pro Gly Thr Ala Ala Trp Thr Thr Ser Ser Leu Ala Cys Ala Gln Gly Pro Glu Phe Trp Cys Gln Ser Leu Glu Gln Ala
                                                        200
TTG CAG TGC AGA GCC CTA GGG CAT TGC CTA CAG GAA GTC TGG GGA CAT GTG GGA GCC GAT GAC CTA TGC CAA GAG TGT GAG GAC ATC GTC
Leu Gln Cys Arg Ala Leu Gly His Cys Leu Gln Glu Val Trp Gly His Val Gly Ala Asp Asp Leu Cys Gln Glu Cys Glu Asp Ile Val
                                                                    300
CAC ATC CTT AAC AAG ATG GCC AAG GAG GCC ATT TTC CAG GAC ACG ATG AGG AAG TTC CTG GAG CAG GAG TGC AAC GTC CTC CCC TTG AAG
His Ile Leu Asn Lys MET Ala Lys Glu Ala Ile Phe Gln Asp Thr MET Arg Lys Phe Leu Glu Gln Glu Cys Asn Val Leu Pro Leu Lys
                                                                                400
CTG CTC ATG CCC CAG TGC AAC CAA GTG CTT GAC GAC TAC TTC CCC CTG GTC ATC GAC TAC TTC CAG AAC CAG ATT GAC TCA AAC GGC ATC
Leu Leu MET Pro Gln Cys Asn Gln Val Leu Asp Asp Tyr Phe Pro Leu Val Ile Asp Tyr Phe Gln Asn Gln Ile Asp Ser Asn Gly Ile
                                                                                                500
TGT ATG CAC CTG GGC CTG TGC AAA TCC CGG CAG CCA GAG CCA GAG CAG GAG CCA GGG ATG TCA GAC CCC CTG CCC AAA CCT CTG CGG GAC
Cys MET His Leu Gly Leu Cys Lys Ser Arg Gln Pro Glu Pro Glu Gln Glu Pro Gly MET Ser Asp Pro Leu Pro Lys Pro Leu Arg Asp
                                                                                                                600
CCT CTG CCA GAC CCT CTG CTG GAC AAG CTC GTC CTC CCT GTG CTG CCC GGG GCC CTC CAG GCG AGG CCT GGG CCT CAC ACA CAG GAT CTC
Pro Leu Pro Asp Pro Leu Leu Asp Lys Leu Val Leu Pro Val Leu Pro Gly Ala Leu Gln Ala Arg Pro Gly Pro His Thr Gln Asp Leu
```

FIG. 4-1

```
TCC GAG CAG CAA TTC CCC ATT CCT CTC CCC TAT TGC TGG CTC TGC AGG GCT CTG ATC AAG CGG ATC CAA GCC ATG ATT CCC AAG GGT GCG
Ser Glu Gln Gln Phe Pro Ile Pro Leu Pro Tyr Cys Trp Leu Cys Arg Ala Leu Ile Lys Arg Ile Gln Ala MET Ile Pro Lys Gly Ala
            200 201

        700
CTA CGT GTG GCA GTG GCC CAG GTG TGC CGC GTG GTA CCT CTG GTG GCG GGC GGC ATC TGC CAG TGC CTG GCT GAG CGC TAC TCC GTC ATC
Leu Arg Val Ala Val Ala Gln Val Cys Arg Val Val Pro Leu Val Ala Gly Gly Ile Cys Gln Cys Leu Ala Glu Arg Tyr Ser Val Ile

                    800
CTG CTC GAC ACG CTG CTG GGC CGC ATG CTG CCC CAG CTG GTC TGC CGC CTC GTC CTC CGG TGC TCC ATG GAT GAC AGC GCT GGC CCA AGG
Leu Leu Asp Thr Leu Leu Gly Arg MET Leu Pro Gln Leu Val Cys Arg Leu Val Leu Arg Cys Ser MET Asp Asp Ser Ala Gly Pro Arg

                                900
TCG CCG ACA GGA GAA TGG CTG CCG CGA GAC TCT GAG TGC CAC CTC TGC ATG TCC GTG ACC ACC CAG GCC GGG AAC AGC AGC GAG CAG GCC
Ser Pro Thr Gly Glu Trp Leu Pro Arg Asp Ser Glu Cys His Leu Cys MET Ser Val Thr Thr Gln Ala Gly Asn Ser Ser Glu Gln Ala
287

                                            1000
ATA CCA CAG GCA ATG CTC CAG GCC TGT GTT GGC TCC TGG CTG GAC AGG GAA AAG TGC AAG CAA TTT GTG GAG CAG CAC ACG CCC CAG CTG
Ile Pro Gln Ala MET Leu Gln Ala Cys Val Gly Ser Trp Leu Asp Arg Glu Lys Cys Lys Gln Phe Val Glu Gln His Thr Pro Gln Leu

                                                            1100
CTG ACC CTG GTG CCC AGG GGC TGG GAT GCC CAC ACC ACC TGC CAG GCC CTC GGG GTG TGT GGG ACC ATG TCC AGC CCT CTC CAG TGT ATC
Leu Thr Leu Val Pro Arg Gly Trp Asp Ala His Thr Thr Cys Gln Ala Leu Gly Val Cys Gly Thr MET Ser Ser Pro Leu Gln Cys Ile

                                                                 1200
CAC AGC CCC GAC CTT TGA TGAGAACTCAG CTGTCCAGAA AAAGACACGT CCTTTAAAAT GCTGCAGTAT GGCCAGACAG TGGTGGCTCA CACCTGCAAT CCCAGC
His Ser Pro Asp Leu End
                381

ACCT TAGGAGGCCG AGGCAGGAGG ATCC
```

FIG. 4-2

CANINE SP5

```
         10         20    N term         40         50          C term
MDVGSKEVLI ESPPDYSAAP RGRLGIPCFP SSLKRLLIIV VVIVLVVVVI VGALLMGLHM

         70         80         90        100        110        120
SQKHTEMVLE MSMGGPEAQQ RLALQERVGT TATFSIGSTG IVVYDYQRLL IAYKPAPGTC

        130        140        150        160        170        180
CYIMKMTPEN IPSLEALTRK FQDFQVKPAV STSKLGQEEG HDAGSASPGD PLDFLGTTVS

        190
TLCGEVPLFY I.
```

FIG. 5

HUMAN VS. DOG SP18

```
        10        20        30        40        50        60
MAESHLLQWLLLLLPTLCGPGTAAWTTSSLACAQGPEFWCQSLEQALQCRALGHCLQEVW
     :: : ::::::::: : : :   ::::: :: :::::::::::::::::::::::
     LL-W-LLLLPTLCGLGAADWSAPSLACARGPAFWCQSLEQALQCRALGHCLQEVW

        70        80        90       100       110       120
GHVGADDLCQECEDIVHILNKMAKEAIFQDTMRKFLEQECNVLPLKLLMPQCNQVLDDYF
:   :::::::: ::: :: :: :::::::  ::::: :: ::::::: :::   :  ::
GNARADDLCQECQDIVRILTKMTKEAIFQDMVRKFLEHECDVLPLKLLTPQCHHMLGTYF

       130       140       150       160       170       180
PLVIDYFQNQIDSNGICMHLGLCKSRQPEPEQEPGMSDPLPKPLRDPLPDPLLDKLVLPV
: : :::: ::    :: ::::::   ::::::   ::::            :::: :: 
PVVVDYFQSQINPKIICKHLGLCKPGLPEPEQESELSDPL------------LDKLILPE

                    H2N-
       190       200|      210       220       230       240
LPGALQARPGPHTQDLSEQQFPIPLPYCWLCRALIKRIQAMIPKGALRVAVAQVCRVVPL
::::::   ::::::::::: ::::::::::: ::::::::::::: : : : ::: ::::
LPGALQVT-GPHTQDLSEQQLPIPLPYCWLCRTLIKRIQAMIPKGVLAVTVGQVCHVVPL

                                          COO-
       250       260       270       280       290
VAGGICQCLAERYSVILLDTLLGRMLPQLVCRLVLRCSMDDSAGPRSPTG--EWLPRDSE
: ::::::: ::: : ::: :::::::::::: ::::::  :::::       :: :  : 
VVGGICQCLGERYTVLLLDALLGRMLPQLVCGLVLRCSHEDSAGPALASLPSEWSPQESK

       310       320       330       340       350
CHLCMSVTTQAGNSSEQAIPQAMLQACVGSWLDREKCKQFVEQHTPQLLTLVPRGWDAHT
: ::: ::::::: :::: :::  :::  ::::: :: ::::: : : ::   : ::::
CQLCMFVTTQAGNHSEQATPQAIRQACLSSWLDRQKCEQFVEQHMPRLQTLASGGRDAHT

       370       380
TCQALGVCGTMSSPLQCIHSPDL.
:::::: : :  ::::::: : 
TCQALGACRTTFSPLQCIHIPHF.
```

FIG. 6

```
                                            10                                                    20
NH2-Met Glu Lys Lys Ile Thr Gly Tyr Thr Thr Val Asp Ile Ser Gln Trp His Arg Lys Glu
    ATG GAG AAA AAA ATC ACT GGA TAT ACC ACC GTT GAT ATA TCC CAA TGG CAT CGT AAA GAA
                                            30                                                    40
    His Phe Glu Ala Phe Gln Ser Val Ala Gln Cys Thr Tyr Asn Gln Thr Val Gln Leu Asp
    CAT TTT GAG GCA TTT CAG TCA GTT GCT CAA TGT ACC TAT AAC CAG ACC GTT CAG CTG GAT
                                            50                                                    60
    Ile Thr Ala Phe Leu Lys Thr Val Lys Lys Asn Lys His Lys Phe Tyr Pro Ala Phe Ile
    ATT ACG GCC TTT TTA AAG ACC GTA AAG AAA AAT AAG CAC AAG TTT TAT CCG GCC TTT ATT
                                            70                                                    80
    His Ile Leu Ala Arg Leu Met Asn Ala His Pro Glu Phe Arg Met Ala Met lYs Asp Gly
    CAC ATT CTT GCC CGC CTG ATG AAT GCT CAT CCG GAA TTC CGT ATG GCA ATG AAA GAC GGT
                                            90                                                    100
    Glu Leu Val Ile Trp Asp Ser Val His Pro Cys Tyr Thr Val Phe His Glu Gln Thr Glu
    GAG CTG GTG ATA TGG GAT AGT GTT CAC CCT TGT TAC ACC GTT TTC CAT GAG CAA ACT GAA
                                            110                                                   120
    Thr Phe Ser Ser Leu Trp Ser Glu Tyr His Asp Asp Phe Arg Gln Phe Leu His Ile Tyr
    ACG TTT TCA TCG CTC TGG AGT GAA TAC CAC GAC GAT TTC CGG CAG TTT CTA CAC ATA TAT
CAT                                         130                                                   140
    Ser Gln Asp Val Ala Cys Tyr Gly Glu Asn Leu Ala Tyr Phe Pro Lys Gly Phe Ile Glu
    TCG CAA GAT GTG GCG TGT TAC GGT GAA AAC CTG GCC TAT TTC CCT AAA GGG TTT ATT GAG
                                            150                                                   160
    Asn Met Phe Phe Val Ser Ala Asn Pro Trp Val Ser Phe Thr Ser Phe Asp Leu Asn Val
    AAT ATG TTT TTC GTC TCA GCC AAT CCC TGG GTG AGT TTC ACC AGT TTT GAT TTA AAC GTG
                                            170                                                   180
    Ala Asn Met Asp Asn Phe Phe Ala Pro Val Phe Thr Met Gly Lys Tyr Tyr Thr Gln Gly
    GCC AAT ATG GAC AAC TTC TTC GCC CCC GTT TTC ACC ATG GGC AAA TAT TAT ACG CAA GGC
                                            190                                                   200
    Asp Lys Val Leu Met Pro Leu Ala Ile Gln Val His His Ala Val Cys Asp Gly Phe His
    GAC AAG GTG CTG ATG CCG CTG GCG ATT CAG GTT CAT CAT GCC GTT TGT GAT GGC TTC CAT
                                            210
    Val Gly Arg Met Leu Asn Glu Leu Gln Gln Ser Glu Pro Glu Phe Glu
    GTC GGC AGA ATG CTT AAT GAA TTA CAA CAG TCG GAT CCG GAA TTC GAA
                220                                     230
    Arg Ser Ser Cys Phe Gly Gly Arg Met Asp Arg Ile Gly Ala Gln Ser Gly Leu Gly Cys
    CGC TCT TCT TGT TTC GGT GGT CGT ATG GAT CGT ATC GGT GCT CAA TCT GGT TTG GGT TGT
hANP(102-126)   240
    Asn Ser Phe Arg Tyr-COOH
    AAC TCT TTC AGA TAC
```

FIG. 7

```
                                                           100
CTAGTTAACTAGTACGCAAGTTCACGTAAAAAGGGTATCACAT ATG GAG AAA AAA ATC ACT GGA
                                            MET Glu Lys Lys Ile Thr Gly

TAT ACC ACC GTT GAT ATA TCC CAA TGG CAT CGT AAA GAA CAT TTT GAG GCA TTT
Tyr Thr Thr Val Asp Ile Ser Gln Trp His Arg Lys Glu His Phe Glu Ala Phe

                                             200
CAG TCA GTT GCT CAA TGT ACC TAT AAC CAG ACC GTT CAG CTG GAT ATT ACG GCC
Gln Ser Val Ala Gln Cys Thr Tyr Asn Gln Thr Val Gln Leu Asp Ile Thr Ala

TTT TTA AAG ACC GTA AAG AAA AAT AAG CAC AAG TTT TAT CCG GCC TTT ATT CAC
Phe Leu Lys Thr Val Lys Lys Asn Lys His Lys Phe Tyr Pro Ala Phe Ile His

                                 300
ATT CTT GCC CGC CTG ATG AAT GCT CAT CCG GAA TTC CGT ATG GCA ATG AAA GAC
Ile Leu Ala Arg Leu MET Asn Ala His Pro Glu Phe Arg MET Ala MET Lys Asp

GGT GAG CTG GTG ATA TGG GAT AGT GTT CAC CCT TGT TAC ACC GTT TTC CAT GAG
Gly Glu Leu Val Ile Trp Asp Ser Val His Pro Cys Tyr Thr Val Phe His Glu

                        400
CAA ACT GAA ACG TTT TCA TCG CTC TGG AGT GAA TAC CAC GAC GAT TTC CGG CAG
Gln Thr Glu Thr Phe Ser Ser Leu Trp Ser Glu Tyr His Asp Asp Phe Arg Gln

TTT CTA CAC ATA TAT TCG CAA GAT GTG GCG TGT TAC GGT GAA AAC CTG GCC TAT
Phe Leu His Ile Tyr Ser Gln Asp Val Ala Cys Tyr Gly Glu Asn Leu Ala Tyr

            500
TTC CCT AAA GGG TTT ATT GAG AAT ATG TTT TTC GTC TCA GCC AAT CCC TGG GTG
Phe Pro Lys Gly Phe Ile Glu Asn MET Phe Phe Val Ser Ala Asn Pro Trp Val

AGT TTC ACC AGT TTT GAT TTA AAC GTG GCC AAT ATG GAC AAC TTC TTC GCC CCC
Ser Phe Thr Ser Phe Asp Leu Asn Val Ala Asn MET Asp Asn Phe Phe Ala Pro

600
GTT TTC ACC ATG GGC AAA TAT TAT ACG CAA GGC GAC AAG GTG CTG ATG CCG CTG
Val Phe Thr MET Gly Lys Tyr Tyr Thr Gln Gly Asp Lys Val Leu MET Pro Leu

                                                            700
GCG ATT CAG GTT CAT CAT GCC GTT TGT GAT GGC TTC CAT GTC GGC AGA ATG CTT
Ala Ile Gln Val His His Ala Val Cys Asp Gly Phe His Val Gly Arg MET Leu

                ◄── CAT |        linker         | SP-C ──►
AAT GAA TTA CAA CAG |TCG GAT CCG GAA TTC AAC |GGC ATT CCC TGC TGC CCA GTG
Asn Glu Leu Gln Gln |Ser Asp Pro Glu Phe Asn |Gly Ile Pro Cys Cys Pro Val

                                                 800
CAC CTG AAA CGC CTT CTT ATC GTG GTG GTG GTG GTG GTC CTC ATC GTC GTG GTG
His Leu Lys Arg Leu Leu Ile Val Val Val Val Val Val Leu Ile Val Val Val

                                             848
ATT GTG GGA GCC CTG CTC ATG GGT CTC CAC TAA GCT T
Ile Val Gly Ala Leu Leu MET Gly Leu His End
```

FIG. 8

```
                      BamHI
pC149SP-C           (GGATCC)GGAATTCAAATATTCTGAAATGAGCTGTTGACAATTAATCATCGAA

                                                              100
CTAGTTAACTAGTACGCAAGTTCACGTAAAAAGGGTATCACAT ATG GAG AAA AAA ATC ACT GGA
                                            MET Glu Lys Lys Ile Thr Gly

TAT ACC ACC GTT GAT ATA TCC CAA TGG CAT CGT AAA GAA CAT TTT GAG GCA TTT
Tyr Thr Thr Val Asp Ile Ser Gln Trp His Arg Lys Glu His Phe Glu Ala Phe

                                           200
CAG TCA GTT GCT CAA TGT ACC TAT AAC CAG ACC GTT CAG CTG GAT ATT ACG GCC
Gln Ser Val Ala Gln Cys Thr Tyr Asn Gln Thr Val Gln Leu Asp Ile Thr Ala

TTT TTA AAG ACC GTA AAG AAA AAT AAG CAC AAG TTT TAT CCG GCC TTT ATT CAC
Phe Leu Lys Thr Val Lys Lys Asn Lys His Lys Phe Tyr Pro Ala Phe Ile His

                                 300
ATT CTT GCC CGC CTG ATG AAT GCT CAT CCG GAA TTC CGT ATG GCA ATG AAA GAC
Ile Leu Ala Arg Leu MET Asn Ala His Pro Glu Phe Arg MET Ala MET Lys Asp

GGT GAG CTG GTG ATA TGG GAT AGT GTT CAC CCT TGT TAC ACC GTT TTC CAT GAG
Gly Glu Leu Val Ile Trp Asp Ser Val His Pro Cys Tyr Thr Val Phe His Glu

                        400
CAA ACT GAA ACG TTT TCA TCG CTC TGG AGT GAA TAC CAC GAC GAT TTC CGG CAG
Gln Thr Glu Thr Phe Ser Ser Leu Trp Ser Glu Tyr His Asp Asp Phe Arg Gln

TTT CTA CAC ATA TAT TCG CAA GAT GTG GCG TGT TAC GGT GAA AAC CTG GCC TAT
Phe Leu His Ile Tyr Ser Gln Asp Val Ala Cys Tyr Gly Glu Asn Leu Ala Tyr

             500
TTC CCT AAA GGG TTT ATT GAG AAT ATG TTT TTC GTC TCA GCC AAT CCC GAA TTC
Phe Pro Lys Gly Phe Ile Glu Asn MET Phe Phe Val Ser Ala Asn Pro Glu Phe

 3'-ccg taa ggg agg agg ggt cac gtg-5'
AAC GGC ATT CCC TGC TGC CCA GTG CAC CTG AAA CGC CTT CTT ATC GTG GTG GTG
Asn Gly Ile Pro Cys Cys Pro Val His Leu Lys Arg Leu Leu Ile Val Val Val

    600
GTG GTG GTC CTC ATC GTC GTG GTG ATT GTG GGA GCC CTG CTC ATG GGT CTC CAC
Val Val Val Leu Ile Val Val Val Ile Val Gly Ala Leu Leu MET Gly Leu His

   653
T(AA GCT T)
End HindIII
```

FIG. 9

SYNTHETIC HUMAN 5KD PROTEIN (FULL LENGTH)

SYNTHETIC HUMAN 5KD PROTEIN (FULL LENGTH)

SYNTHETIC HUMAN SP-5 (28-59)

SYNTHETIC HUMAN SP-5 (30-59)

SYNTHETIC D5K #1 [Ser-28, Ser-29 hSP-5 (24-59)]

D5K #2

D5K #3

REC. HUMAN SP-C vs REC. Cys-->Ser SP-C

SP-C; di Ser-Leu

DNA ENCODING AND EXPRESSION SYSTEMS FOR ALVEOLAR SURFACTANT PROTEINS

CROSS-REFERENCE TO RELATED APPLICATIONS

This application is a division of application Ser. No. 07/524,360, filed Jun. 17, 1990, now U.S. Pat. No. 5,104,853, which is a continuation-in-part of U.S. patent application Ser. No. 07/266,443, abandoned, filed Nov. 1, 1988, which is a continuation-in-part of U.S. patent application Ser. No. 07/117,099, abandoned, filed Nov. 4, 1987, which is a continuation-in-part of U.S. patent application Ser. No. 07/008,453, abandoned, filed Jan. 29, 1987, which is a continuation-in-part of U.S. patent application Ser. No. 06/857,715,U.S. Pat. No. 4,933,280, filed Apr. 30, 1986, which is a continuation-in-part of U.S. patent application Ser. No. 06/808,843,U.S. Pat. No. 4,912,038, filed Dec. 13, 1985 which is a continuation-in-part of U.S. patent application Ser. No. 06/680,358, U.S. Pat. No. 4,659,805, filed Dec. 11, 1984.

TECHNICAL FIELD

The invention relates generally to alveolar surfactant proteins (ASP) which are useful in the management of certain respiratory diseases.

BACKGROUND ART

The human lung is composed of a large number of small sacs or alveoli in which gases are exchanged between the blood and the air spaces of the lung. In healthy individuals, this exchange is mediated by the presence of a protein-containing surfactant complex which is synthesized in the microsomal membranes of type II alveolar cells. In the absence of adequate levels of this complex, a lung cannot properly function—i.e., the alveoli collapse during exhalation, and cannot be subsequently re-inflated by inhaling. Thus, the untreated inability to synthesize this complex may result in death or in severe physical damage if left untreated.

The best documented instance of inadequate surfactant complex levels occurs in premature infants and infants born after complicated pregnancies, and is widely known as respiratory distress syndrome (RDS). A widely publicized form of this syndrome has been designated hyaline membrane disease, or idiopathic RDS. RDS is currently the leading cause of infant mortality and morbidity in the United States and in other developed countries, and substantial efforts have been directed to diagnosis and treatment. Current treatment has focused on mechanical (pressure) ventilation which, at best, is an invasive stop-gap measure that often results in damage to the lung and other deleterious side effects, including complications such as bronchopulmonary dysplasia, interstitial emphysema and pneumothorax. Mental retardation has also resulted on occasion when this treatment was used (Hallman, M., et al, *Pediatric Clinics of North America* (1982) 29:1057–1075).

Limited attempts have been made to treat the syndrome by surfactant substitution. This would be a method of choice, as, in general, only one administration is required, and the potential for damage is reduced. For example, Fujiwara, et al, *Lancet* (1980) 1:55-used a protein-depleted surfactant preparation derived from bovine lungs, while Hallman, M., et al, *Pediatrics* (1983) 71:473–482 used a surfactant isolated from human amniotic fluid to treat a limited number of infants with some success. U.S. Pat. No. 4,312,860 to Clements discloses an artificial surfactant which contains no protein and is said to be useful in this approach although no data are shown. In short, surfactant substitution has not been widely used clinically.

The preferred surfactant substitute would be the lung surfactant complex itself. This complex is composed of apoprotein, two phospholipids (dipalmitoyl phosphocholine (DPPC) and phosphatidyl-glycerol (PG)) which are present in major amount, several lipid components present in only very minor amount, and calcium ions. The apoprotein contains proteins having molecular weights of the order of 32,000 daltons and very hydrophobic proteins of the order of about 10,000 daltons (King, R. J. et al, *Am J Physiol* (1973) 224:788–795). The 32,000 dalton protein is glycosylated and contains hydroxyproline.

A major reason for the limited progress in surfactant replacement therapy has been the lack of availability of the protein portion of the complex. Replacement therapies have focused on attempts to use the lipid components alone, and it appears that the performance of such treatment can be markedly improved by addition of the apoprotein (Hallman, M., et al, *Pediatric Clinics of North America* (1982) (supra)). At present, however, these proteins are available only from normal adult human lung, and from amniotic fluid. Even efficient isolation procedures would not provide an adequate supply. Thus, it would be desirable to have available a method for producing practical quantities of apoprotein for use alone or in conjunction with the saturated phospholipid portion of the complex.

Related PCT patent application W086/03408 describes the recombinant production of the human ASP protein of about 32 kd, the retrieval of DNA sequences encoding various canine ASP proteins and the retrieval of a single representative of the human ASP protein group of about 10 kd molecular weight. It is now clear that efficient production of the "10K" group is required for use in adequate therapy.

The additional related PCT patent application W087/06588, published Nov. 5, 1987, gives further description of these 10K proteins and their encoding DNAs. FIGS. 1 and 2 of that application show the full-length cDNAs encoding precursors of canine and human SP-18-derived protein. The mature human protein is described to begin at the phenylalanine residue encoded at codon 201 of sthe full-length sequence. The construction of vectors for expression of the SP-18 precursor in both mammalian and bacterial cells is described in detail. Expression of the full-length precursor in mammalian cells yielded 43 kd and 25 kd precursor proteins as determined on SDS-PAGE. The 25 kd product is stated to be the glycosylated form of a 181 amino acid sequence spanning Phe-201 Glu-381 encoded in this sequence. Certain modified forms of the human protein to provide cleavage sites which may be helpful in providing more uniform production of mature forms of the precursor are also described. Bacterial expression of the SP-18 cDNA is also described.

FIGS. 5 and 6 of PCT application W087/06588 show the DNA and deduced amino acid sequences of two cDNA clones encoding the precursors for the smaller molecular weight 5 kd-8 kd proteins, designated SP-5. Like the SP-18 cDNA, these clones are disclosed to encode a precursor for the smaller 5 kd-8 kd proteins isolated. The putative N-terminus is stated to be Phe or Gly at codons 24 and 25 of this sequence; it is postulated that the mature C-terminus of these proteins is at Gln-108 for the 8 kd protein and Glu-80 or Thr-65 for the 5 kd protein. Expression of this cDNA in mammalian and bacterial cells is also described.

The disclosures of the two above-cited PCT applications, W086/03408 and W087/06588, are incorporated herein by reference.

The present application describes various SP-5-related peptides which are effective as lung surfactant proteins. These SP-5 analogs and fragments can be prepared by chemical synthesis or by recombinant methods and offer specific members of the repertoire of lung surfactant proteins useful in treatment of respiratory diseases and symptomologies.

The parent application hereto, U.S. application Ser. No. 07/117,009, now abandoned, also describes the 10K group of proteins in some detail. The disclosure of that application is hereby incorporated by reference in its entirety, and reference may be had thereto for material not explicitly described or explained herein. The present application is based on further studies of the human SP-5 protein, and in particular is directed to analogs of that protein which have now been found to have ASP activity. The analogs presently described and claimed, in addition to retaining the stability and biological activity of the native polypeptide, are less susceptible to aggregation than native 5 kd protein.

DISCLOSURE OF THE INVENTION

The invention provides specific forms of human SP-18- and SP-5-derived proteins. Some of these which are analogs of the encoded sequence display substantially reduced aggregation relative to the native protein, i.e., aggregation resulting from various types of intramolecular and intermolecular interaction, primarily covalent, disulfide bonding. These analogs are therefore much easier to extract and purify than the native polypeptide.

The present SP-5-derived peptides result from modifications in both the length and the amino acid sequence of human SP-5, but retain chemical and physical stability as well as the biological activity of the native polypeptide.

In other aspects of the invention, pharmaceutical compositions for treating respiratory distress syndrome are provided, the compositions formulated so as to contain an SP-18- and/or SP-5-related peptide. The invention also encompasses a method of treating respiratory distress syndrome by administration of an SP-18- and-/or SP-5-related peptide.

BRIEF DESCRIPTION OF THE DRAWINGS

FIG. 1 shows the DNA and deduced amino acid sequence of a cDNA encoding human SP-5-derived protein.

FIG. 2 shows an analogous cDNA variant encoding human SP-5-derived protein.

FIG. 3 is the amino acid sequence encoded by codons 1–74 of SP-5 DNA with the N-terminus and C-terminus as marked.

FIG. 4 is the human cDNA#3 encoding the SP-18 precursor protein.

FIG. 5 is the amino acid sequence of the canine 5 kd protein, with the N-terminus and C-terminus as marked.

FIG. 6 illustrates the correlation between the human and canine 18 kd proteins in the 10K ASP mixture.

FIG. 7 shows the DNA and amino acid sequences for chloramphenicol amino transferase (CAT) and human atrial natriuretic protein (hANP).

FIG. 8 shows the protein encoding the insert in pC210SP-C.

FIG. 9 is the BamHI/HindIII insert of pC149SP-C which encodes a CAT-SP-5 fusion protein.

FIGS. 10 and 11 represent control testing done with the full human 5 kd protein, while FIGS. 12 through 18 represent the results obtained with various analogs of the protein.

Modes of Carrying Out the Invention

Definitions

Figure 10:
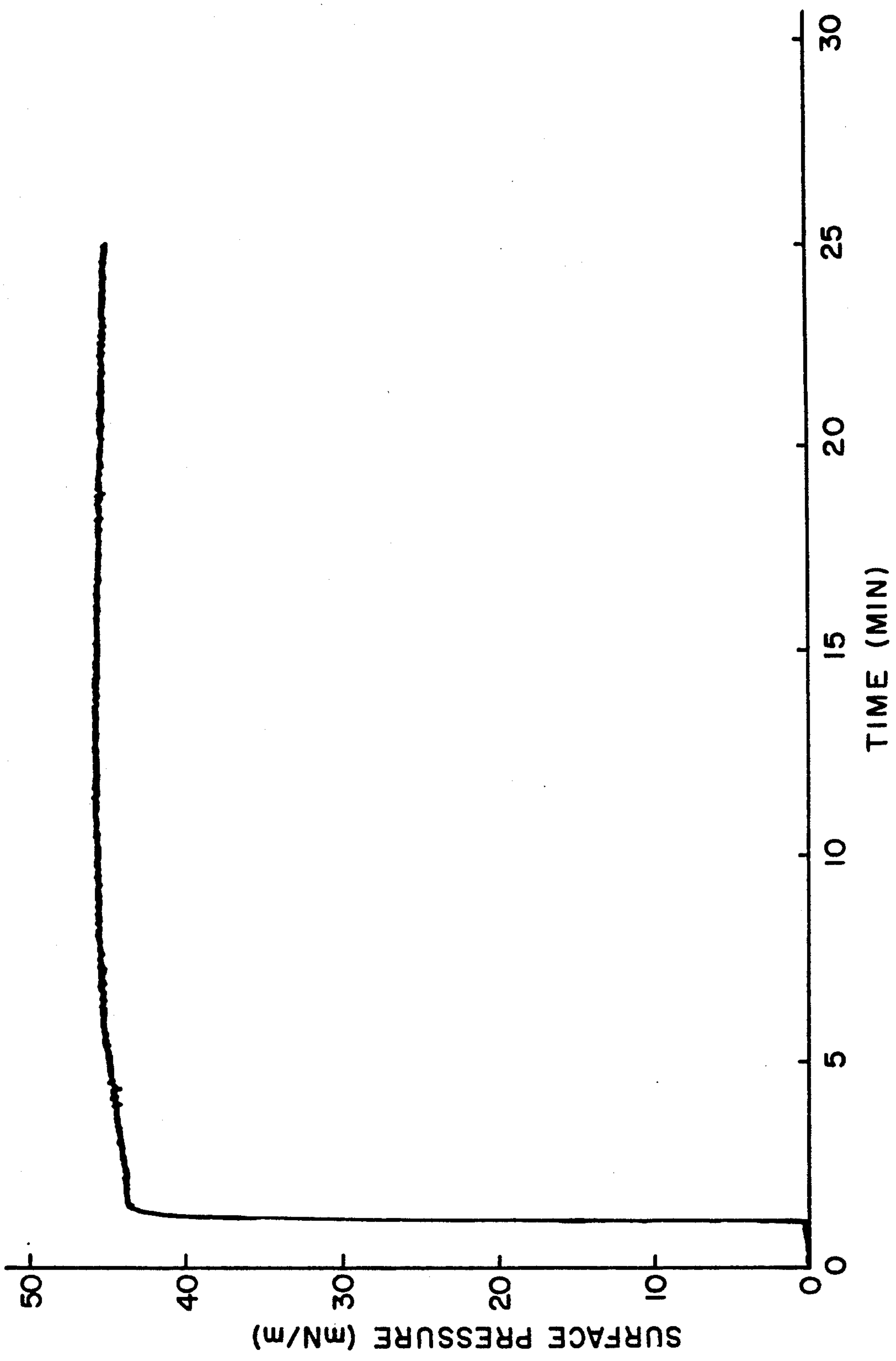
FIGS. 10 through 18 are graphic representations of the in vitro results obtained with various polypeptides in standard tests for ASP activity.

As used herein, "alveolar surfactant protein (ASP)" refers to apoprotein associated with the lung surfactant complex and having ASP activity as defined hereinbelow. The ASP of all species examined appears to comprise one or more components of relatively high molecular weight (of the order of 32 kd) designated herein "32K ASP" and one or more quite hydrophobic components of relatively low molecular weight (of the order of 5–20 kd) designated herein "10K ASP". (King, R. J., et al, *J Appl Physiol* (1977) 42:483–491; Phizackerley, P. J. R., *Biochem J* (1979) 183:731–736.)

Further discussion of the nature of the surfactant proteins known to occur in mammals is found in W087/06588. Briefly, as there described, the "10K" group of proteins is derived from precursors encoded by two different DNAs. One set of these DNAs, designated SP-18, encodes a precursor for proteins which appear at approximately 18 kd on gels, but which show molecular weights of 10 kd under reducing conditions. The other DNA, designated P-5, encodes precursors for proteins which show molecular weights of 8 kd or 5 kd on gels. The invention herein concerns specific peptides related to those generated by the SP-18 and SP-5 precursor proteins.

"ASP activity" for a protein is defined as the ability, when combined with lipids either alone or in combination with other proteins, to exhibit activity in the in vivo assay of Robertson, B., Lung (1980) 158:57–68. In this assay, the sample to be assessed is administered through an endotracheal tube to fetal rabbits or lambs delivered prematurely by Caesarian section. (These "preemies" lack their own ASP, and are supported on a ventilator.) Measurements of lung compliance, blood gases and ventilator pressure provide indices of activity. Preliminary assessment of activity may also be made by an in vitro assay, for example that of King, R. J., et al, *Am J Physiol* (1972) 223:715–726, or that described and illustrated in W087/06588 of Hawgood, et al, which utilizes a straightforward measurement of surface tension at a air-water interface when the protein is mixed with a phospholipid vesicle preparation. All of the SP-18- and SP-5-derived peptides described and claimed herein show ASP activity.

The "hSP-5-derived peptides" of the invention are intended to include polypeptides which are based on the amino acid sequence encoded by the human SP-5 DNA shown in FIGS. 1-2, especially those portions encoding the portion of the precursor amino acid sequence shown in FIG. 3, and which have ASP activity as defined above. These SP-5 peptides are defined by the amino acid sequence $$X—AA_{28}—AA_{29}—AA_{30}—AA_{31}—AA_{32}—AA_{33}—AA_{34}—AA_{35}—$$

Leu—Leu—Ile—Z—Z—Z—Z—Z—Z—Leu—Ile—Z—Z—Z—

-continued

Ile—Z—Gly—Ala—Leu—Leu—Met—Y, wherein:

$AA_{28}$ is Cys or Ser,
$AA_{29}$ is Cys or Ser,
$AA_{30}$ is Pro or Ala,
$AA_{31}$ is Val or Gln,
$AA_{32}$ is His or Lys,
$AA_{33}$ is Leu or Ala,
$AA_{34}$ is Lys or Gln,
$AA_{35}$ is Arg or Gln,
Z is either Val or Ile,
Y is OH, Gly-OH, Gly-Leu-OH, Gly-Leu-His-OH, or Gly-Leu-His-$Y_1$, wherein $Y_1$ is a C-terminal extension sequence of 1–15 amino acids corresponding to amino acids 60–74 in FIG. 3, and
X is H or an amino acid sequence selected from the group consisting of H-$AA_{27}$-, H-$AA_{26}$-$AA_{27}$-, or X'-$AA_{26}$-$AA_{27}$-, wherein:

$AA_{27}$ is Pro or Ala,
$AA_{26}$ is Ile or Ser, and
X' is H or an N-terminal extension sequence of 1–25 amino acids corresponding to amino acids 1–25 in FIG. 3, or the pharmaceutically acceptable salts or amides thereof, with the proviso that if X is Phe-Gly-Ile-Pro, Y is His-$Y_1$ wherein $Y_1$ is a C-terminal extension of amino acids 60–66 and all Z are Val, $AA_{28}$-$AA_{35}$ cannot be-Cys-Cys-Pro-Val-His-Leu-Lys-Arg-.

Preferred embodiments of Y in hSP-5-derived peptides within the aforementioned group are those wherein Y is Gly-Leu-OH or Gly-Leu-His-$Y_1$ wherein $Y_1$ is the C-terminal extension corresponding to the 15 amino acids numbered 60–74 in FIG. 3. Preferred embodiments of X are those wherein X is H, H-$AA_{27}$-, H-$AA_{26}$-$AA_{27}$-, Gly-$AA_{26}$-$AA_{27}$- or Phe-Gly-$AA_{26}$-$AA_{27}$-.

And as will be discussed below, particularly preferred SP-5 analogs within the aforementioned group are those wherein both $AA_{28}$ and $AA_{29}$ are Ser. While not wishing to be bound by any theory, the inventors demonstrate herein that replacement of the two native Cys residues at these positions with Ser reduces intramolecular and intermolecular disulfide bonding and thus, correspondingly, reduces protein aggregation.

The "hSP-18-derived peptides" of the invention include peptides having the amino acid sequences shown in FIG. 4, which shows human clone #3, spanning positions 201 to a carboxy terminus at positions 275–281. Particularly preferred is the SP-18 protein spanning positions 201–279.

Production of the Protein

The shorter forms of the hSP-18 and hSP-5-derived peptides of the invention can be prepared by solid phase peptide synthesis or by other standard peptide synthetic means. These peptides are also conveniently produced using recombinant vectors and hosts.

Most of the techniques which are used to construct vectors, transform cells, effect expression in transformed cells and the like are widely practiced in the art, and most practitioners are familiar with the standard resource materials which describe specific conditions and procedures. Illustrative methods as they apply to the peptides of the invention are set forth with particularity in W086/03408 and W087/06588.

Expression may be achieved in a variety of host systems including, in particular, mammalian and bacterial systems, as well as yeast-based systems. In addition, other cell systems have become available in the art, such as the baculovirus vectors used to express protein encoding genes in insect cells. The expression systems set forth below are illustrative, and it is understood by those in the art that a variety of expression systems can be used.

As the nucleotide sequences encoding the various hSP-5- and hSP-18-derived peptides are available through retrieval of cDNA or genomic DNA and/or using synthesis methods, these may be expressed in this variety of systems. If procaryotic systems are used, an intronless coding sequence should be used, along with suitable control sequences. The cDNA clones for any of the above ASP proteins may be excised with suitable restriction enzymes and ligated into procaryotic vectors for such expression, or synthetic coding sequences may be used. For procaryotic expression of ASP genomic DNA, the DNA should be modified to remove the introns, either by site-directed mutagenesis, or by retrieving corresponding portions of cDNA and substituting them for the intron-containing genomic sequences. The intronless coding DNA is then ligated into expression vectors for procaryotic expression.

As exemplified, either genomic, cDNA, or synthetic (or partially synthetic) ASP-encoding sequences may also be used directly in an expression system capable of processing introns, usually a mammalian host cell culture. To effect such expression, the genomic or other sequences can be ligated downstream from a controllable mammalian promoter which regulates the expression of these sequences in compatible cells.

In addition to recombinant production, proteins of the invention of sufficiently short length, such as the proteins related to the SP-5-encoded protein, may be prepared by standard protein synthesis methods.

Protein Recovery

The ASP protein may be produced either as a mature protein or a fusion protein, or may be produced along with a signal sequence in cells capable of processing this sequence for secretion. It is sometimes advantageous to obtain secretion of the protein, as this minimizes the difficulties in purification; thus it is preferred to express the human ASP gene which includes the codons for native signal sequence in cells capable of appropriate processing. It has been shown that cultured mammalian cells are able to cleave and process heterologous mammalian proteins containing signal sequences, and to secrete them into the medium (McCormick, F., et al, *Mol Cell Biol* (1984) 4:166).

When secreted into the medium, the ASP protein is recovered using standard protein purification techniques. The purification process is simplified, because relatively few proteins are secreted into the medium, and the majority of the secreted protein will, therefore, already be ASP. However, while the procedures are more laborious, it is well within the means known in the art to purify this protein from sonicates or lysates of cells in which it is produced intracellularly in fused or mature form. One such method is illustrated below.

Assay for ASP Activity

In vitro methods have been devised to assess the ability of ASP proteins to function by reducing surface tension (synonymous with increasing surface pressure) to generate a film on an aqueous/air interface. Studies using these methods have been performed on the isolated native 10K canine ASP (Benson, B. J., et al *Prog Resp Res* (1984) 18:83-92; Hawgood, S., et al, *Biochemistry* (1985) 24:184-190). These methods are also applied to the individual synthetic and recombinant peptides. Since the function of the surfactant complex in vivo is to create a film at the air/aqueous interface in order to reduce surface tension, the ability of ASP proteins to enhance the formation of the film created by the spread of lipid or lipoprotein at such a surface in an in vitro model is clearly relevant to its utility.

An in vivo model, described in detail in Section D.10 of W087/06588, is also employed.

Administration and Use

The purified proteins and analogs can be used alone and in combination in pharmaceutical compositions appropriate for administration for the treatment of respiratory distress syndrome in infants or adults. The compositions of the invention are also useful in treating related respiratory diseases such as pneumonia and bronchitis. The complex contains about 50% to almost 100% (wt/wt) lipid and 50% to less than 1% ASP; preferably ASP is 5%-20% of the complex. The lipid portion is preferably 70%-90% (wt/wt) DPPC with the remainder unsaturated phosphatidyl choline, phosphatidyl glycerol, triacylglycerols, palmitic acid, palmitoyl oleyl phosphoglyceride (POPG), or mixtures thereof. The complex is assembled by mixing a solution of ASP with a suspension of lipid liposomes, or by mixing the lipid protein solutions directly in the presence of detergent or an organic solvent. The detergent or solvent may then be removed by dialysis or evaporation.

While it is possible to utilize the natural lipid component from lung lavage in constructing the complex, and to supplement it with appropriate amounts of ASP proteins, the use of synthetic lipids is clearly preferred. First, there is the matter of adequate supply, which is self-evident. Second, purity of preparation and freedom from contamination by foreign proteins, including infectious proteins, which may reside in the lungs from which the natural lipids are isolated, are assured only in the synthetic preparations. Of course, reconstitution of an effective complex is more difficult when synthetic components are used.

Preferred ASP compositions comprise either complexes with the isolated 10K mixture, the SP-5- or SP-18-encoded proteins alone, active SP-5 analogs, alone or in combination, a complex of the 10K and 32K mixtures, or a complex of an SP-18 or SP-5-related protein and the 32K mixture. In the latter case, a preferred protein ratio—i.e., 32K: 10K or 32K:SP-18 or 32K:SP-5—is typically in the range of 3:1 to 200:1, preferably about 10:1 to 5:1. The 32K protein may be added directly to an aqueous suspension of phospholipid vesicles in an aqueous solution. Because it is so hydrophobic, the 10K protein is added to the lipids in an organic solvent, such as chloroform, the solvents evaporated, and the vesicles re-formed by hydration.

The addition of the 32K protein to the 10K type for the administration of the surfactant complex appears to have a synergistic effect—i.e., the combination of 32K and 10K type proteins exerts the desired activity at protein concentrations lower than those required for the 10K protein alone. Accordingly, in a preferred method of the invention, the surfactant complex administered will contain an effective amount of the 10K mixture, or of the individual SP-5 or SP-18 proteins, or the hSP-5 or hSP-18-derived peptides of the invention in admixture with the 32K ASP. Of course, mixtures of the individual hSP-5 or hSP-18-derived peptides can be used. Particularly preferred compositions contain the ratios of 32K: 10K type protein as set forth above, along with a suitable amount of lipid component, typically in the range of 50% to almost 100% of the total composition.

The compositions containing the complex are preferably those suitable for endotracheal administration, i.e., generally as a liquid suspension, as a dry powder "dust" or as an aerosol. For direct endotracheal administration, the complex is suspended in a liquid with suitable excipients such as, for example, water, saline, dextrose, or glycerol and the like. The compositions may also contain small amounts of nontoxic auxiliary substances such as pH buffering agents, for example, sodium acetate or phosphate. To prepare the "dust", the complex, optionally admixed as above, is lyophilized, and recovered as a dry powder.

If to be used in aerosol administration, the complex is supplied in finely divided form along with an additional surfactant and propellent. Typical surfactants which may be administered are fatty acids and esters, however, it is preferred, in the present case, to utilize the other components of the surfactant complex, DPPC and PG. Useful propellants are typically gases at ambient conditions, and are condensed under pressure. Lower alkanes and fluorinated alkanes, such as Freon, may be used. The aerosol is packaged in a container equipped with a suitable valve so that the ingredients may be maintained under pressure until released.

The surfactant complex is administered, as appropriate to the dosage form, by endotracheal tube, by aerosol administration, or by nebulization of the suspension or dust into the inspired gas. Amounts of complex between about 0.1 mg and 200 mg, preferably 50-60 mg/kg body weight, are administered in one dose. For use in newly born infants, one administration is generally sufficient. For adults, sufficient reconstituted complex is administered to replace demonstrated levels of deficiency (Hallman, M., et al, *J Clinical Investigation* (1982) 70:673-682).

In addition, one or more ASP proteins, including the hSP-18- and hSP-5-derived peptides described herein can be used as a carrier or vehicle for the delivery of other biologically active and important molecules to the lung and/or through the lung to the blood vasculature. In the latter case, delivery of agents important for other organs in the body can be effected.

It is to be understood that while the invention has been described in conjunction with the preferred specific embodiment thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

Preparation A

Isolation of Mammalian ASP Proteins

Canine, human and bovine ASP proteins were obtained in purified form as described in W086/03408 and W087/06588, and DNA encoding the 32K protein for human and dog and DNA encoding the SP-18 protein of human and dog were recovered and disclosed in these applications. Two variants of the complete cDNA sequence encoding the SP-5 precursor proteins for human ASP were recovered, as described in W087/06588 and are reproduced as FIGS. 1 and 2 herein.

EXAMPLE 1

Identification of N- and C-Termini of the Isolated 10K Proteins

The 5 kd Protein

The carboxyl terminus of the 5 kd protein in the 10K mixture is difficult to ascertain, as the protein is derived from a large precursor having a molecular weight of about 20,500 daltons. Mass spectrometric analysis of isolated native canine protein indicated the apparent carboxyl terminus to be His-59, as shown in the amino acid sequence for the canine protein in FIG. 5. Amino acid sequence analysis of enzymatic cleavage fragments of native SP-5 protein isolated from human lung lavage fluid has indicated a carboxyl terminus at Leu-58 (see Johansson, J. et al., FEBS Letters, 232, No. 1 (1988), 61–64). Reanalysis of the native canine and native human forms of SP-5 by mass spectrometry has indicated that the molecular weights observed are consistent with species having a carboxyl terminus at Leu-58 in which the cysteine residues (at AA-28 in the canine and AA-28,29 in the human forms) are palmitylated via thioester bonds. Treatment of the native forms with reducing agent to remove the palmityl groups, followed by mass spectrometric analysis and HPLC analysis confirmed the presence of these species. Accordingly, preferred analogs of the present invention may have a carboxyl terminus at either Leu-58 or His-59 as shown in FIGS. 1, 2 and 3. Using recombinant production techniques, the inventors herein have produced SP-5 analogs having carboxyl terminii at both Leu-58 and His-59 and shown them to be essentially equivalent in both the in vitro and in vivo assays described herein. In particular, analogs which have been demonstrated to be comparatively equivalent are the human SP-5 analog proteins having an amino terminus as Gly-25, Ser residues at AA-28 and AA-29, and a carboxyl terminus at either Leu-58 or His-59.

The N-terminus of the human 5 kd protein was determined by direct amino acid sequencing to be phenylalanine (at position 24 as shown in FIG. 3), but truncated species were also found having glycine at 25 and isoleucine at 26 as alternative N-termini.

The 18 kd Protein

The carboxy terminus of the 18 kd protein in the 10K mixture was analyzed using quantitative amino acid composition, amino acid sequencing of the protein beginning at the N-terminus, carboxypeptidase Y digestion (an enzyme which cleaves amino acids from the C-terminus of proteins), and mass spectrometry. FIG. 6 shows the amino acid sequences of the human and canine proteins.

Sequence analysis of the canine and bovine 18 kd proteins, after cleavage at methionine with cyanogen bromide, indicated the C-terminus of the canine protein to be His-279 and that of the bovine protein to be Ser-278. Enzymatic analysis using carboxypeptidase Y gave Leu-275 as the C-terminus of both the canine and bovine proteins. Mass spectral analysis of the canine protein showed the C-terminus at Arg-276 with a minor sequence extending to His-279, as predicted by amino acid sequencing after cyanogen bromide cleavage. In sum, the carboxy terminus is near His-279 in the canine protein, and, by analogy, near Met-279 in the human 18 kd protein. Based on the aforementioned results, there appear to be truncated C-terminal forms of the protein as well as truncated or staggered N-termini, depending on the particular preparation and species. It is accordingly postulated by the inventors herein that there are probably a number of C-termini for a particular species. As seen in FIG. 6, the putative N-terminus for the human protein is the phenylalanine at position 201 as described in W087/06588. The carboxy terminus approximates the methionine codon at position 279, as also shown in FIG. 6.

Preparation B

Vector Construction for Mammalian Expression

The hSP-18-derived proteins and hSP-5-derived proteins disclosed herein can be prepared using recombinant techniques. Vectors suitable for expression of the various ASP-encoding sequences in mammalian cells, which are also capable of processing intron-containing DNA, were constructed. In these vectors, expression is controlled by the metallothionein II (hMTII) control sequences, as described in W087/06588. This published application describes in detail the preparation of host vectors pMT, pMT-Apo, pMT-SV(9), pMT-SV(10) and pMT-Apo10. All of these vectors have insertion sites which permit a coding sequence to placed under control of the metallothionein promoter. Those vectors including "Apo" in their designation also contain the 3' terminal regulatory signals associated with the ApoAI gene downstream of the insert region; those containing "9" or "10" in their designation also contain operable SV-40 viral enhancers.

As described in the published application, pMTApo10 was digested with BamHI, blunted and ligated to the cDNA sequences obtained from the clone #3 of 1275 bp encoding SP-18 precursor, as a blunted fragment. This was done by isolating an EcoRI/BamHI (partial) fragment from cDNA #3 avoiding the BamHI site at nucleotide 663 and subcloning into EcoRI/BamHI-digested pUC9. The desired fragment was excised with EcoRI and HindIII, blunted with Klenow, and then inserted into pMTApo10. The resulting vector, pMT(E):SP-18-40k, was transformed into CHO cells. Induction of the promoter in cultures of these transformed cells resulted in production of 25 kd and 43 kd proteins which are immunoprecipitated with antisera raised against human 18 kd ASP. When subjected to Western blot using antisera raised against a peptide spanning residues 336–353 of the precursor, the 25 kd and 43 kd proteins were detected. It is believed the 25 kd product represents a 181 amino acid sequence spanning Phe-201:Leu-381, containing a N-linked glycosylation site.

As further described in W087/06587, analogous vectors were constructed, including SP-18-encoding DNA, using standard site-specific mutagenesis techniques to provide sites for in vitro cleavage of the precursor protein which was, apparently, produced in CHO cells from the full length sequence In one such construct, the 381 amino acid precursor was modified to replace each of the Gln-199:Gln-200 and Arg-286:Ser-187 by Asn:Gly, to provide sites cleavable by hydroxylamine (which cleaves between Asn and Gly). Cleavage of the precursor thus produced with hydroxylamine generates the putative mature form, with an additional gly residue at the amino terminus, and with the putative carboxy-terminal Arg-286 changed to an Asn residue. In another construct, Phe-201 and Ser-87 are changed to Asp residues. Cleavage with acid (between Asp and Pro) yields a mature form of the SP-18 protein missing the N-terminal Phe-201, and with an additional carboxy-terminal Asp residue. An additional construct allows in vitro processing of the precursor with a more gentle enzymatic procedure, employing Staph V8 peptidase, which cleaves after Glu residues. Advantage is taken of natural Glu residues at Glu-198 and Glu-291 by converting the Glu-251 to Asp. The 43 kd precursor is cleaved with Staph V8 to yield the putative mature SP-18 protein with an additional Gln-Gln at the amino terminus, and Pro-Thr-Gly-Glu at the carboxy terminus. In an additional construct, Glu residues can be placed in positions 200 and/or 287.

In a similar manner, the blunted EcoRI insert of the SP-5 clones of FIGS. 1 and 2 was placed into BamHI digested pMT-Apo10 to obtain pMT(E):SP-5 vectors, and transformed into CHO cells.

EXAMPLE 2

Mammalian Expression of DNA Encoding hSP-18- and hSP-5-Derived Peptides

DNA sequences encoding the hSP-5- and hSP-18-derived proteins of the invention described herein are placed into BamHI-digested pMT-Apo10 to obtain the appropriate expression vectors. Preferably, the DNA encoding the desired protein is ligated in operable linkage to a signal sequence effective in CHO cells. Transformation into CHO cells and expression of the inserted sequences is conducted as described as follows.

Chinese hamster ovary (CHO)-K1 cells are grown on medium composed of a 1:1 mixture of Coon's F12 medium and DME21 medium with 10% fetal calf serum. The competent cells are co-transformed with the vector of interest and pSV2:NEO (Southern, P., et al, *J Mol Appl Genet* (1982) 1:327-341). pSV2:NEO contains a functional gene conferring resistance to the neomycin analog G418. In a typical transformation, 0.5 $\mu$g of pSV2:NEO and 5 $\mu$g or more of the expression vector DNA are applied to a 100 mm dish of cells. The calcium phosphate-DNA co-precipitation according to the protocol of Wigler, M., et al, *Cell* (1979) 16:777-785, is used with the inclusion of a two minute "shock" with 15% glycerol in PBS after four hours of exposure to the DNA.

Briefly, the cells are seeded at 1/10 confluence, grown overnight, washed 2× with PBS, and placed in 0.5 ml Hepes-buffered saline containing the $CaPO_4$·DNA co-precipitate for 15 min and then fed with 10 ml medium. The medium is removed by aspiration and replaced with 15% glycerol in PBS for 1.5-3 min. The shocked cells are washed and fed with culture medium. Until induction of MT-II-controlled expression, the medium contains F12/DMEM21 1:1 with 10% FBS. A day later, the cells are subjected to 1 mg/ml G418 to provide a pool of G418-resistant colonies. Successful transformants, also having a stable inheritance of the desired plasmid, are then plated at low density for purification of clonal isolates.

The transformants are assayed for production of the desired protein, first as pools, and then as isolated clones in multi-well plates. The plate assay levels are somewhat dependent on the well size—e.g. results from 24 well plates are not directly comparable with those from 96 well plates. Clones which are found by plate assay to be producing the protein at a satisfactory level can then be grown in production runs in roller bottles. Typically, the levels of production are higher when the scale-up is done. For this reason, typically 100-200 or more individual clones are assayed by various screening methods on plates and 5-10 of the highest producers are assayed under production conditions (roller bottle).

Pools of transformed cells are grown in multi-well plates and then exposed to $5\times10^{-5}$ to $1\times10^{-4}$ zinc ion concentration to induce production of the desired ASP protein.

Semiconfluent monolayers of individual cell lines growing in McCoy's 5A medium with 10% FBS are washed with phosphate-buffered saline (PBS) and refed with McCoy's containing 10% FBS, $1\times10^{-4}$ zinc chloride, and 0.25 mM sodium ascorbate. (Ascorbate may be helpful in mediating the hydroxylation of proline residues.) Twenty-four hours post induction, the cells are washed with PBS and refed with serum-free McCoy's containing the zinc chloride and ascorbate. After 12 hours, the conditioned media are harvested.

Preparation C

Bacterial Expression Vectors

As set forth in W087/06588, the unglycosylated forms of the ASP proteins can be produced in bacteria. For SP-18 proteins, the gene can be expressed, for example, to produce a 181 amino acid precursor representing met-preceded residues 201-381 or as a hydroxylamine-cleavable fusion protein precursor with a 15 residue betagalactosidase leader. A modified cDNA #3 encoding amino acids 201-381 of the cDNA, preceded by ATG is inserted into the Trp-controlled vector pTrp-233, described in W087/06588, between the EcoRI site and the HindIII site to give pTrp-20. This construct produces a protein of M.W. 20 kd. An analogous construct in the pBGal host vector, pBGal-20, contains the same sequences of SP-18 cDNA #3 fused to a 15 residue beta-galactosidase leader through a hydroxylamine-sensitive Asn-Gly doublet, and produces a fusion protein of MW=22 kd.

The pTrp-20 and pBGal-20 plasmids are used to transform *E. coli* W3110 to ampicillin resistance. Rapidly growing cultures of pTrp-20/W3110 or pBGal-20/W3110 in M9 medium (1×M9 salts, 0.4% glucose, 2 mg/ml thiamine, 200 $\mu$g/ml $MgSO_4 \cdot 7H_2O$, 0.5% casamino acids, are treated with 100 $\mu$g/ml IAA (3-beta-indoleacrylate, Sigma I-1625) to induce the trp promoter.

W087/06588 also describes vectors encoding modified SP-18 protein sequences providing cleavage sites for expression in bacteria. In pTrp-20, codons encoding Arg-286:Ser-287 were altered to encode Asn-Gly; introducing the hydroxylamine-sensitive cleavage site, or the codon for Ser-287 was replaced by a codon for Asp, resulting in the acid-sensitive Asp-Pro cleavage site, or the codon for Glu-251 was replaced with a codon for Asp, allowing cleavage with Staph V8 at Glu-291 without cleaving the desired protein. These constructs would be expected to generate SP-18 having the amino acid sequence of 287-381 or 291-381. Also, in both pTrp-20 and pBGal-20, the sequences 3' to the putative carboxy terminal Arg-286 were deleted and replaced by a stop codon, putatively generating peptides representing SP-18 codon positions 201-286. Neither construct resulted in labeled protein of proper size after induction, however.

With respect to SP-5-derived proteins W087/06588 describes, analogous to pTrp-20, the insertion of the fragment of the cDNA #18 extending from Gly-25 preceded by ATG to Ile-197 of the Sp-5 "precursor" into EcoRI/HindIII digested pTrp-233 to give pTrp-5 and into the pBGal host vector to give pBGal-5 wherein the SP-5 sequence is fused to a beta-galactosidase leader through a hydroxylamine-sensitive Asn-Gly. These vectors putatively generate SP-5-derived proteins spanning 25–197. Also, cleavage with Staph V8 of the protein expected from this construct at the Glu preceding Phe-24 and at Glu-66 would yield an SP-5-derived peptide spanning positions 24–66.

All these constructs are transformed into *E. coli* W3110 and expressed as described above.

EXAMPLE 3

Production of hSP-18 and hSP-5 Derived Proteins in Bacteria

It may be advantageous to express the hSP-18- and hSP-5-derived peptides as a cleavable fusion protein with an upstream stabilizing sequence. U.S. Ser. No. 231,224 filed Aug. 11, 1988, now abandoned, assigned to the same assignee, and incorporated herein by reference, describes the construction of several vectors which contain a portion of the chloramphenicol acetyltransferase (CAT)-encoding gene joined to DNA encoding a specified portion of the hSP-18 or hSP-5 peptides. Exemplified are vectors encoding 35 amino acids of an SP-5-derived peptide, i.e., hSP-5(24-59) joined to CAT through a 6 amino acid linker, Ser-Asp-Pro-Glu-Phe-Asn. As described in the above-referenced application. These vectors are prepared as follows.

The vectors including the SP-18- and SP-5-derived proteins are obtained from a host vector constructed with an insert encoding human atrial natriuretic peptide (hANP). This intermediate vector, pChNF109, is constructed as follows.

Expression vector pChNF109 encodes a 241 amino acid CAT-hANP hybrid protein containing an endoproteinase Glu-C proteolytic cleavage site. The DNA and encoded amino acid sequences of CAT and hANP are shown in FIG. 7. Most of the CAT gene (amino acids 1–210) has been joined in-frame to the hANP (102–126) gene and cleavage site (26 amino acids) through a linker sequence (5 amino acids). This vector was constructed from plasmids pTrp233, pCAT21, and phNF75 which supplied the plasmid backbone and trp promoter-operator, the CAT gene, and the hANP (102–126) gene and cleavage site, respectively.

Plasmid pTrp233 was described in W087/06588. Plasmid pCAT21 was constructed by insertion of the CAT gene (from transposon Tn9, Alton and Vapnek, *Nature* (1979) 282:864–869) into pTrp233 under the control of the trp promoter-operator. Plasmid pAL13ATCAT (a plasmid containing Tn9, disclosed in co-pending U.S. Ser. No. 095,742, filed Sep. 11, 1987, now abandoned, and incorporated herein by reference) was digested with NdeI and HindIII and the approximately 750 bp NdeI-HindIII fragment containing the CAT gene (with the initiating Met residue encoded at the NdeI site) was purified using agarose gel electrophoresis. The CAT gene was ligated with NdeI/HindIII-digested pTrp233 using T4 DNA ligase, and the resulting plasmid pCAT21 was isolated from *E. coli* MC1061.

Plasmid phNF75 was constructed by insertion of a synthetic hANP gene preceded by a proteolytic cleavage site into plasmid pBgal (Shine et al, *Nature* (1980) 285:456). Eight oligodeoxyribonucleotides were assembled into a synthetic hANP(102–126) gene preceded by an endoproteinase Glu-C cleavage site. The synthetic gene was ligated into BamHI-digested pTrp233. A plasmid with the insert in the orientation which gives adjacent HindIII, BamHI and EcoRI sites at the 3′ end of the hANP gene, phNF73, was identified by the size of the fragments generated by digestion with HindIII and PvuII. Plasmid phNF73 was digested with EcoRI, the hANP gene purified using polyacrylamide gel electrophoresis, and the gene ligated into EcoRI-digested pBgal to obtain phNF75.

Expression vector pChNF109 was constructed by insertion of DNA fragments containing CAT, hANP and the proteolytic cleavage site, and a linker sequence into plasmid pTrp233. Plasmid phNF75 was digested with EcoRI and HindIII, the approximately 80 bp EcoRI-HindIII fragment containing hANP was purified by polyacrylamide gel electrophoresis, and ligated into EcoRI/HindIII-digested pTrp233 to obtain phNF87. pCAT21 was digested with ScaI, and BamHI synthetic linkers (5′-CGGATCCG-3′) were attached to the blunt termini. The ligation was digested with BamHI and the approximately 740 bp BamHI fragment was purified by agarose gel electrophoresis. The BamHI cassette and BamHI-digested plasmid phNF87 were ligated to obtain pChNF109 having the CAT gene fused in-frame to the endoproteinase Glu-C cleavage site followed by the hANP gene.

By replacing the hANP encoding sequences in pChNF109 with SP-5 and SP-18 sequences, human SP-5- and SP-18-derived peptides are expressed as fusions with portions of bacterial CAT. The surfactant peptides are joined to the carboxy terminus of the CAT sequences through a hydroxylamine-sensitive asparagine-glycine linkage. The CAT-surfactant fusions are expressed from the tryptophan promoter of the bacterial vector pTrp233.

Expression Vector pC210SP-B

SP-18 expression vector pC210SP-B encodes a fusion protein of 293 residues in which 210 amino acids of CAT are joined to the 76 amino acids of SP-18 through a linker of 7 amino acids containing the hydroxylamine-sensitive cleavage site. Cleavage of the fusion with hydroxylamine releases a 77 amino acid SP-18 product containing 76 residues of SP-18, plus an amino-terminal glycine residue.

To construct pC210SP-B, the short EcoRI-HindIII segment containing hANP sequences was removed from pChNF109, and replaced by a portion of human SP-18 cDNA #3 (FIG. 3) extending from the PstI site at nucleotide (nt) 643 to the SphI site at nt 804. The EcoRI site was joined at the PstI site through two complementary oligonucleotides encoding the hydroxylamine sensitive cleavage site as well as the amino-terminal residues of mature SP-18 (oligo #2307: 5′-AAT TCA ACG GTT TCC CCA TTC CTC TCC CCT ATT GCT GGC TCT GCA-3′ and oligo #2308: 5′-GAC CCA GCA ATA GGG GAG AGG AAT GGG GAA ACC GTT G-3′). The SphI site was joined to the HindIII site of pTrp233 through a second set of complementary nucleotides encoding the carboxy-terminal residues of the SP-18 peptide (oligo #3313: 5′-AGC TTA CCG GAG GAC GAG GCG GCA GAC CAG CTG GGG CAG CAT G-3′ and oligo #3314: 5′-CTG CCC CAG CTG GTC TGC CGC CTC GTC CTC CGG TA-3′).

The expression plasmid was used to transform *E. coli* stain W3110 to ampicillin resistance. Rapidly growing cultures of pC210SP-B/W3110 in M9 medium were made 25 μg/ml IAA (3-beta indoleacrylate, Sigma I-1625) to induce the trp promoter. By 1 hr after induction, refractile cytoplasmic inclusion bodies were seen by phase contrast microscopy inside the still-growing cells. 5 hr after induction, the equivalent of 1 $O.D._{550}$ of cells were pelleted by centrifugation, then boiled for 5 min in SDS sample buffer for electrophoresis in a 12% SDS-polyacrylamide gel followed by staining with Coomassie Blue. The predicted molecular weight of the CAT:SP-18 fusion protein is 45,000 daltons. The hybrid CAT:SP-18 protein was estimated to comprise 15–20% of the total cell protein in the induced cultures.

pC210SP-C

An amino acid sequence of a 251 residue fusion protein is encoded in plasmid pC210SP-C. The 210 amino acids of CAT are joined to 35 amino acids of mature SP-5 through a linker of 6 amino acids. The SP-5 comprises 14% of the total fusion.

In FIG. 8 is shown the nucleotide sequence of the insert in pC210SP-C, in which the EcoRI-HindIII fragment of pC210SP-B containing SP-18 sequences has been replaced by a segment of human SP-5 cDNA #18 extending from the ApaLI site at nucleotide 123 to the AvaII site at nucleotide 161. The EcoRI site of the CAT vector was joined to the SP-5 ApaLI site through two complementary oligonucleotides encoding the hydroxylamine sensitive cleavage site as well as the amino-terminal residues of mature SP-5 (oligo #2462: 5'-AAT TCA ACG GCA TTC CCT GCT GCC CAG-3' and oligo #2463: 5'-TGC ACT GGG CAG CAG GGA ATG CCG TTG-3'). The AvaII site of SP-5 was joined to the HindIII site of pC210SP-B through a second set of complementary nucleotides encoding the carboxy-terminal residues of mature SP-5 and a stop codon (oligo #2871: 5'-AGC TTA GTG GAG ACC CAT GAG CAG GGC TCC CAC AAT CAC CAC GAC GAT GAG-3' and oligo #2872: 5'-GTC CTC ATC GTC GTG GTG ATT GTG GGA GCC CTG CTC ATG GGT CTC CAC TA-3').

pC179SP-C

The amino acid sequence of the 217 residue fusion protein encoded by pC179SP-C is a slight modification of the sequence shown in FIG. 8. In pC179SP-C, the 179 amino acids of CAT are joined to 35 amino acids of mature SP-5 through a linker of 3 amino acids (Glu, Phe, Asn). SP-5 comprises 16% of the total fusion.

To construct pC179SP-C, a portion of the CAT sequence was removed from pC210SP-C. Starting with pC210SP-C, a DNA fragment extending from the NcoI site at nt 603 (FIG. 8) to the EcoRI site at nt 728 was removed, and the NcoI and EcoRI cohesive ends were rejoined with two complementary oligonucleotides (oligo #3083: 5'-CAT GGG CAA ATA TTA TAC GCA AG-3' and oligo #3084: 5'-AAT TCT TGC GTA TAA TAT TTG CC-3'). In effect, 31 residues of CAT, and 3 residues of the linker polypeptide are missing in the new fusion protein encoded by vector pC179SP-C.

pC149SP-C

The amino acid sequence of the 187 residue fusion protein encoded by pC149SP-C is a slight modification of the sequence shown in FIG. 8. In plasmid pC149SP-C, the 149 amino acids of CAT are joined to 35 amino acids of SP-5 through a linker of 3 amino acids (Glu, Phe, Asn). SP-5 comprises 18.7% of the total fusion.

To construct pC149SP-C, a portion of the CAT segment of pC210SP-C extending from the DdeI site at nt 523 (FIG. 8) to the EcoRI site at nt 728 was removed and replaced by a set of two complementary oligonucleotides (oligo #3082: 5'-TCA GCC AAT CCC G-3' oligo #3081: 5'-AAT TCG GGA TTG GC-3'). The resulting sequence is shown in FIG. 9.

pC106SP-C

The amino acid sequence of the 144 residue fusion protein encoded by pC106SP-C is a slight modification of the sequence shown in FIG. 8. In plasmid pC106SP-C, the 106 amino acids of CAT are joined to 35 amino acids of SP-5 through a linker of 3 amino acids (Glu, Phe, Asn). SP-5 comprises 24% of the total fusion.

pC106SP-C was constructed by replacing the EcoRI fragment of pC210SP-C (nt 302 to nt 728, FIG. 8) with two sets of complementary oligos which were annealed, then ligated together through a region of homology (oligo #3079: 5'-AAT TCC GTA TGG CAA TGA AAG ACG GTG AGC TGG TGA TAT GGG ATA GTG TTC ACC CTT GT-3' was annealed with oligo #3085: 5'-ACA CTA TCC CAT ATC ACC AGC TCA CCG TCT TTC ATT GCC ATA CGG-3'; oligo #3080: 5'-TAC ACC GTT TTC CAT GAG CAA ACT GAA ACG TTT TCA TCG CTC TGG G-3' was annealed with oligo #3078: 5'-AAT TCC CAG AGC GAT GAA AAC GTT TCA GTT TGC TCA TGG AAA ACG GTG TAA CAA GGG TGA-3').

Each SP-5 expression vector was used to transform *E. coli* strain W3110 to ampicillin resistance. Rapidly growing cultures of expression strains were induced as described above. By 1 hr after induction, refractile cytoplasmic inclusion bodies were seen by phase contrast microscopy inside the still-growing cells. 5 hr after induction, the equivalent of 1 $O.D._{550}$ of cells were pelleted by centrifugation, then boiled for 5 min in SDS sample buffer for electrophoresis in a 12% SDS-polyacrylamide gel followed by staining with Coomassie Blue. Proteins of the correct MW were obtained from these vectors. The hybrid CAT:SP-5 protein produced by each vector is estimated to comprise 15–20% of the total cell protein in the induced cultures.

Modification of SP-5 DNA

To obtain modified sequences encoding hSP-5 analogs, site-directed mutagenesis can be used. For example, starting with pC149SP-C, the BamHI/HindIII fragment shown in FIG. 9 is excised and cloned into mp8. The insert is then subjected to site-directed mutagenesis using the primer 5'-GTG-CAC-TGG-GGA-GGA-GGG-AAT-GCC-3' as shown in the figure. This results in the codons for cysteine at positions 28 and 29 of the mature protein being converted to codons for serine in these positions. The mutagenized BamHI/HindIII fragment is then isolated and then ligated back into the expression vector pTrp233.

The constructs, for example, C149SP-C or the corresponding mutagenized vector are then transformed into *E. coli* and the transformed cells are cultured using standard techniques. The trp promoter is induced by treatment of the culture with IAA, and expression of the gene encoding the desired SP-5-derived peptide is obtained.

Purification of hSP-5-Derived Peptides

The bacterial cells are then lysed by passage through a homogenizer. The insoluble inclusion bodies released by this treatment are recovered by centrifugation at 5000 rpm for 30 minutes or by filtration through 0.1 micron Millipore Durapore membranes. The resulting inclusion bodies are washed 3× with either 1% Triton X-100 or in 1.0M guanidine hydrochloride, 10 mM EDTA, 20 mM TrisHCl, pH 8.0 and 100 mM collected by centrifugation or filtration as described. The inclusion bodies are solubilized in 20 mM Tris-HCl, pH 8.0, 6M guanidine HCl, 50 mM DTT, at a concentration of 15–25 ng/ml.

After removal of insoluble material by centrifugation the fusion protein containing the SP-5-derived peptide is cleaved by addition of an equal volume of hydroxylamine (2M) in 6M guanidine hydrochloride, 50 mM DTT containing 0.2M $K_2CO_3$. The cleavage is allowed to proceed for 48 hours. The solution is diluted to 1.2M guanidine HCl (5 fold) with 10 mM Tris, pH 8.0, 20 mM DTT. This causes the proteins in the cleavage reaction mix to precipitate; this precipitate is collected by centrifugation.

The SP-5-derived peptide is then extracted from the majority of the remaining protein with a chloroform:methanol (1:1, v:v) solution containing 100 mM DTT. Enough of this solution is added to the precipitate so that the SP-5-derived peptide is 1 mg/ml; and the material is extracted for six hours at room temperature. The extract is then centrifuged to remove insoluble material.

The supernatant from this centrifugation is then mixed with sulfo-propyl cellulose (0.04 ml of sulfo-propyl cellulose) per mg of SP-5 peptide in the extract. The extract is acidified with HCl to bring the concentration to 5 mM. After allowing the SP-5 to bind overnight, the sulfo-propyl cellulose is extensively washed with a buffer containing 19 parts chloroform, 19 parts methanol, and 2 parts 0.1N HCl (wash buffer). Additional washes are performed with a solution of wash buffer adjusted to 50 mM DTT with solid DTT and made 20 mM sodium acetate, pH 4, by addition of a stock solution of 2M Na acetate. The SP-5 peptide is then eluted with wash buffer containing 50 mM DTT and adjusted to 50 mM Na-acetate, pH 6, by adding a stock solution of 2M Na-acetate, pH 6. The SP-cellulose is removed by filtration. The final step of purification is gel permeation chromatography over Sephadex LM-60 using the wash buffer described above as the eluant.

EXAMPLE 4

Synthetic Peptides

Various synthetic peptides based on the human SP-5-encoded mixture have been synthesized using standard techniques. Referring to FIG. 3, the following peptides have been synthesized using solid phase peptide synthesis:

(1) hSP-5(24-74), i.e., beginning at Phe-24 and ending at Gly-74;

(2) hSP-5(34-74), i.e., beginning at Lys-34 and ending at Gly-74; and (3) hSP-5(24-61), i.e., beginning at Phe-24 and ending at Ser-61.

hSP-5(24-74)

Phe—Gly—Ile—Pro—Cys—Cys—Pro—Val—His—Leu—Lys—Arg—
Leu—Leu—Ile—Val—Val—Val—Val—Val—Leu—Ile—Val—Val—Val—Ile—
Val—Gly—Ala—Leu—Leu—Met—Gly—Leu—His—Met—Ser—Gln—Lys—His—
Thr—Glu—Met—Val—Leu—Glu—Met—Ser—Ile—Gly.

hSP-5(34-74)

Lys—Arg—Leu—Leu—Ile—Val—Val—Val—Val—Val—Leu—Ile—
Val—Val—Val—Ile—Val—Gly—Ala—Leu—Leu—Met—Gly—Leu—His—Met—
Ser—Gln—Lys—His—Thr—Glu—Met—Val—Leu—Glu—Met—Ser—Ile—Gly.

hSP-5(24-61)

Phe—Gly—Ile—Pro—Cys—Cys—Pro—Val—His—Leu—Lys—Arg—
Leu—Leu—Ile—Val—Val—Val—Val—Val—Leu—Ile—Val—Val—Val—Ile—
Val—Gly—Ala—Leu—Leu—Met—Gly—Leu—His—Met—Ser.

The synthetic peptides were prepared by standard t-BOC solid-phase peptide synthesis methodology using an Applied Biosystems 430A peptide synthesizer. The protecting groups used were: Cys—4-methyl benzyl; His—Boc; Lys—2-chloroCBZ, Arg—Tosyl. The resin was built up on Boc-Ser(OBzl)-O-PAM resin (0.5 mmol, 0.72 meq/g loading). All residues were single coupled with HOBT estER AND His residues which were double coupled using Boc-His(Boc)-OH as its symmetrical anhydride. Resin was removed prior to addition of Arg at residue 12. This resin can be directly sequenced in a gas phase sequencer at this point, since most of the side chains are not protected, and run as authentic PTH-amino acids. After confirming that the sequence was reasonably homogeneous, the synthesis was completed. The resin was cleaved and all protecting groups removed using standard HF cleavage conditions. To 1 g of peptide-resin was added 1.5 ml anisole, 0.25 ml methyl ethyl sulfide and 15 ml of distilled HF, and cleavage was conducted in a standard Kel-F HF cleavage apparatus. Cleavage was effected at −103C. for 30 min followed by an additional 30 min at 03C. Hf was immediately and rapidly removed in order to minimize aggregation. However, aggregation still occurs to some degree since only very small quantities of the selected peptide can be resolubilized from the cleavage mixture. After removal of HF, the resin-peptide mixture was alternately washed with ether and chloroform and then dried. The peptide cannot be solubilized using standard aqueous extraction but must be separated from resin by solubilizing in MeOH/chloroform/HCl.

After solubilization in 75% trifluoroacetic acid, each of the peptides was purified. A preferred method of purification is gel filtration using LH-60 columns in a solution of chloroform and methanol (1:1 v/v) containing 0.5% HCl. Each of the synthetic peptides was tested for in vitro and in vivo activity as in Example 5.

EXAMPLE 5

Activity of Synthetic Peptides

In vitro and in vivo activity was evaluated using the procedure described in PCT Publication W087/06588, cited supra, at Section D.9 and D.10, respectively.

Peptide 34-74 was ineffective in phospholipid film spreading in vitro, and, as might be expected from this result, was also ineffective in premature rabbit lungs. The N-terminal amino acids would thus appear to be required for maximal activity.

Peptide 24-74, a C-terminal extended peptide, was quite effective in both decreasing the surface tension of an air-water interface in vitro and in effecting reasonable lung function in animals. In Table 1, $P_{ins}$ is a measure of how effective the surfactant formulation is in lowering surface tension in the lungs. This decreased tension is manifested by a decreased pressure of inspired oxygen. Peptide 24-74 was quite effective compared to the saline control solution, and nearly as effective as the rabbit surfactant positive control. It should be noted that the native 5 kd protein is as effective as the surfactant control.

TABLE 1

| | $P_{ins}$ | | | |
|---|---|---|---|---|
| | 10 min. | 20 min. | 30 min. | N |
| Rabbit Surfactant | 25 | 23 | 20 | 6 |
| SP 5K 10:1 | 27 | 22.5 | 20 | 5 |
| 24–74 10:1 | 28 | 24 | 22 | 3 |
| Sodium Chloride | 35 | 34 | 33 | 4 |

$P_{ins}$ values at 10, 20 and 30 minutes refer to the inspiratory pressures (cm $H_2O$) required to maintain tidal volumes in the lung of 6–7 mls/kg body weight. (The lower the pressure on the ventilator, the better.)

Peptide 24-61 was found to be as effective in vivo as native surfactant. In fact, in certain animal experiments, the $P_{ins}$ was lower in the animals treated with 24-61 than in the surfactant control. In all cases, the phospholipid mixture was DPPC:egg PG (7:3, w/w) and the ratio of PL to protein was 10:1. It is preferable that the peptide be administered in conjunction with additional lipids as described infra, and, accordingly, in the studies summarized in Table 2, 10 wt. % palmitic acid was incorporated into the formulations. Thus, the formula was DPPC:PG:Peptide:fatty Acid in a weight ratio of about 10:1:1:1.

TABLE 2

Five different experiments were carried out in vivo. The numbers refer to pressures, $P_{ins}$, at 30 minutes.

| Study # | Surfactant | NaCl | 24–61 |
|---|---|---|---|
| 119 | 22 | 0* | 22 |
| 120 | 16.5 | 26 | 15 |
| 121 | 19 | 33 | 16 |
| 122 | 16.5 | 33 | 15 |
| 123 | 0* | 32 | 15.5 |
| Ave | 18.5 | 31 | 16.7 |

*0 refers to a pneumothorax before the end of the experiment.
In all cases, 24–61 synthetic peptide was mixed with PL:Palmitic acid:syn pep (10:1:1) by weight. The phospholipid (PL) is DPPC:PG (7:3) by weight.

EXAMPLE 6

Additional hSP-5 Peptides

The following SP-5-derived peptides of the invention have been synthesized using the CAT fusion method of Example 3 or by solid phase synthesis and tested for ASP activity:

(1) hSP-5(28-59), i.e., beginning at Cys-28 and ending at His-59;

(2) hSP-5(30-59), i.e., beginning at Pro-30 and ending at His-59;

(3) D5K#1: ($S^{28}$ $S^{29}$-hSP-5(24-59)), i.e., equivalent to hSP-C(24-59), but having serines substituted for the cysteines at positions 28 and 29;

(4) D5K#2: ($A^{27}$ $S^{28}$ $S^{29}$ $A^{30}$-hSP-5(24-59)), i.e., beginning at Phe-24 and ending at His-59, with serines substituted for the cysteines at positions 28 and 29 and alanine substituted for proline at positions 27 and 30; and (5) D5K#3: ($S^{26}$ $A^{27}$ $S^{28}$ $S^{29}$ $A^{30}$ $Q^{31}$ $K^{32}$, $A^{33}$-hSP-5(25-59)), beginning with Gly-25 and ending at His-59, with amino acids 26 through 33 replaced as indicated.

After solubilization, each of the peptides was purified as described above. Each of the synthetic peptides was tested for in vitro and in vivo activity, using the above-described procedures.

Figure 11:
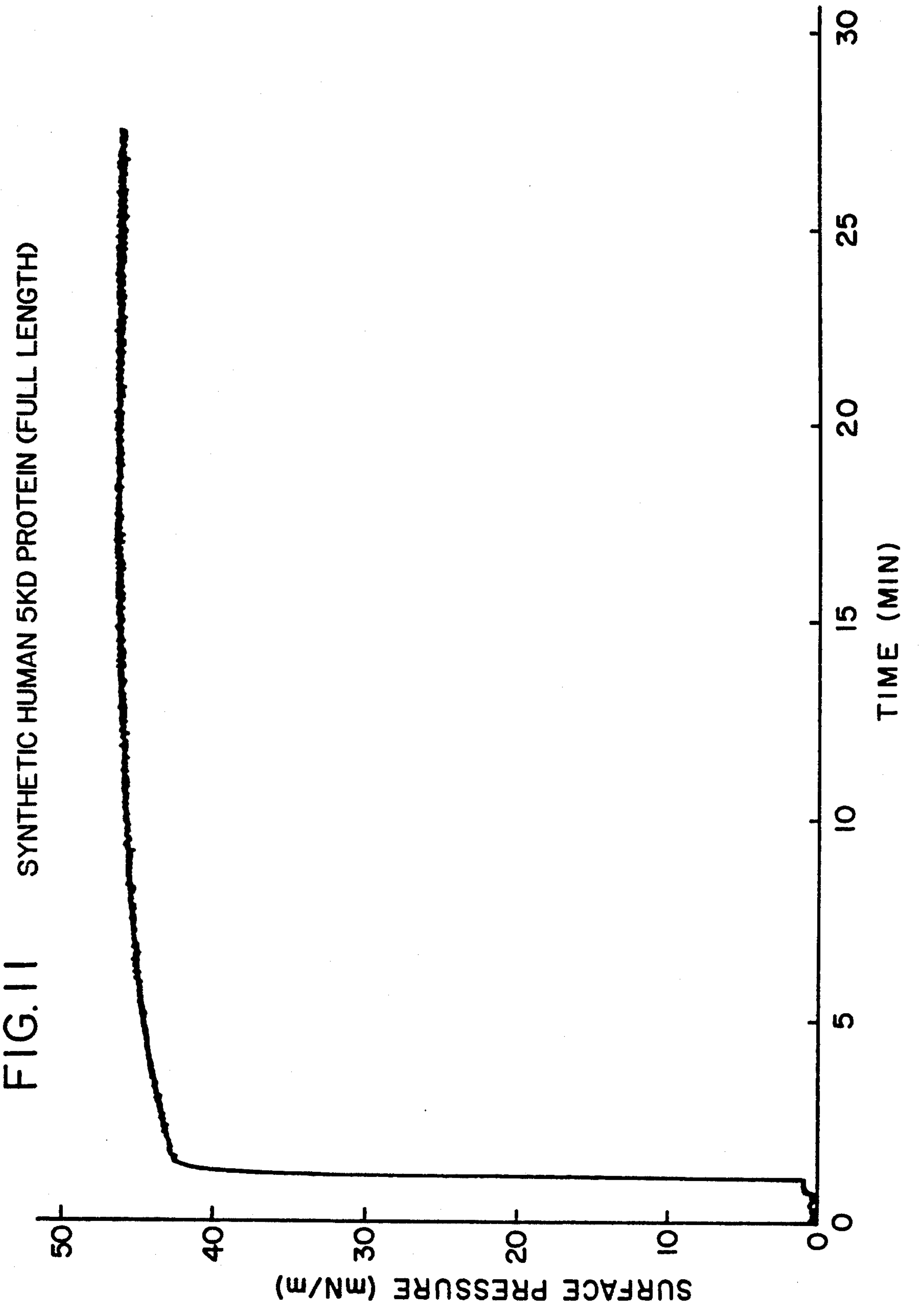

FIG. 10 represents a control, and is a graphic representation of surface pressure versus time obtained with the full length human 5 kd protein formulated with DPPC:PG and palmitate (ratio of DPPC:PG:palmitate:protein approximately 7:3:1:0.5). FIG. 11 is similar, representing the results obtained with the full length human 5 kd protein formulated with the same components (7:3:1:1) and tested at a pH of 7.5 and a temperature of 37° C.

Figure 12:
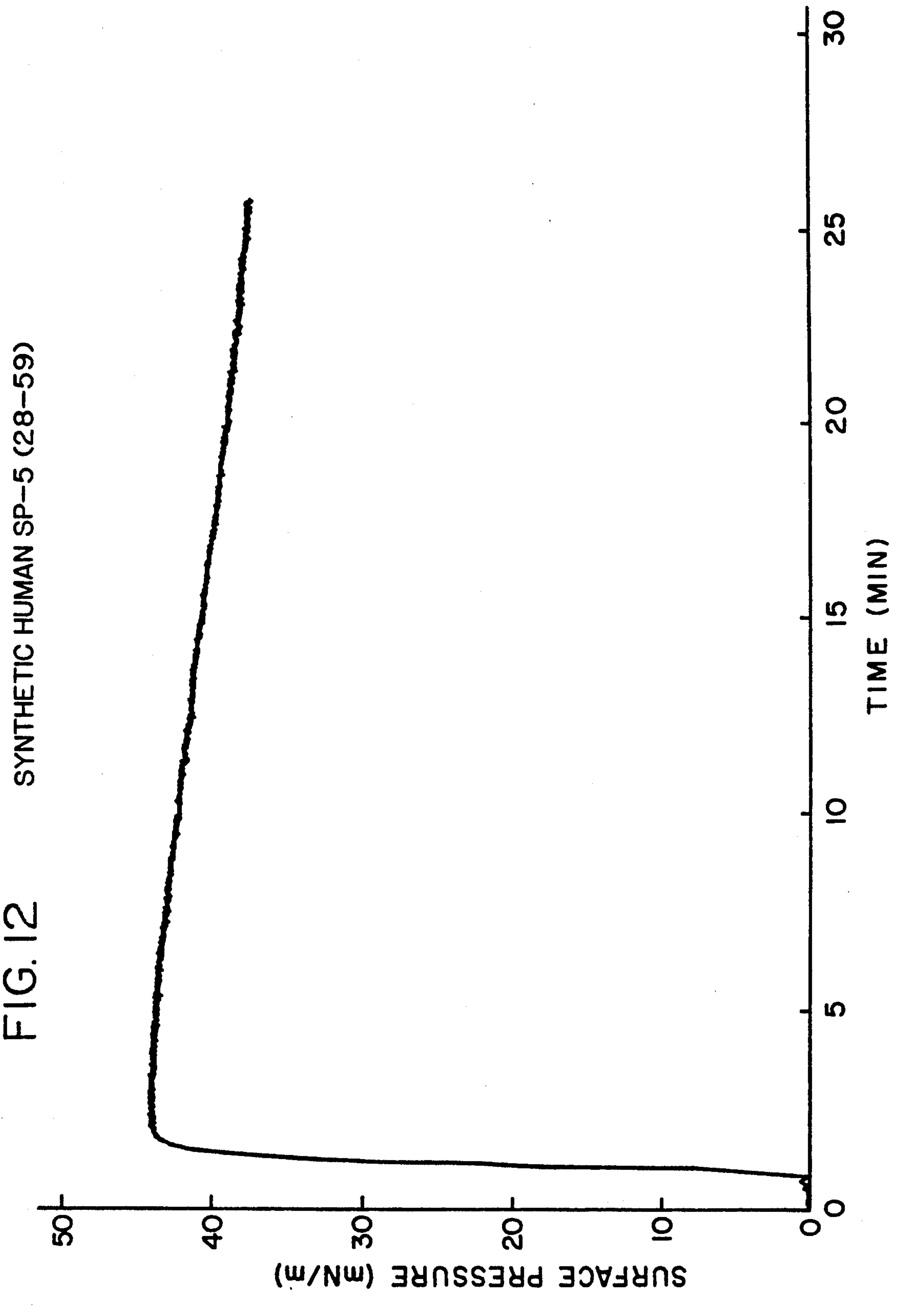

The synthetic peptide hSP-5(28-59), formulated with DPPC:PG and palmitate as in the control experiment represented in FIG. 12, showed an initial rate of spreading identical to that observed with the natural peptide.

Figure 13:
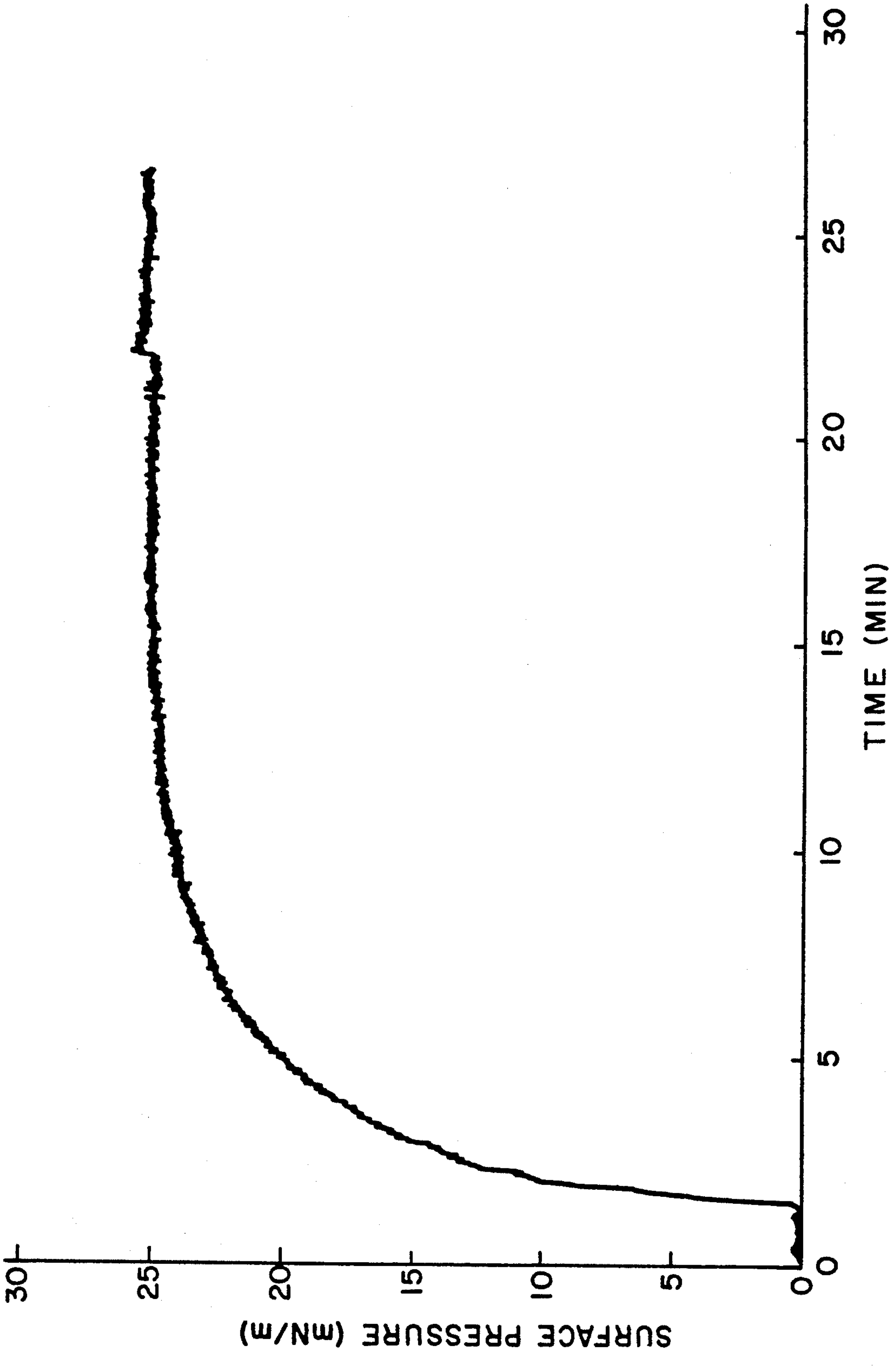
Figure 14:
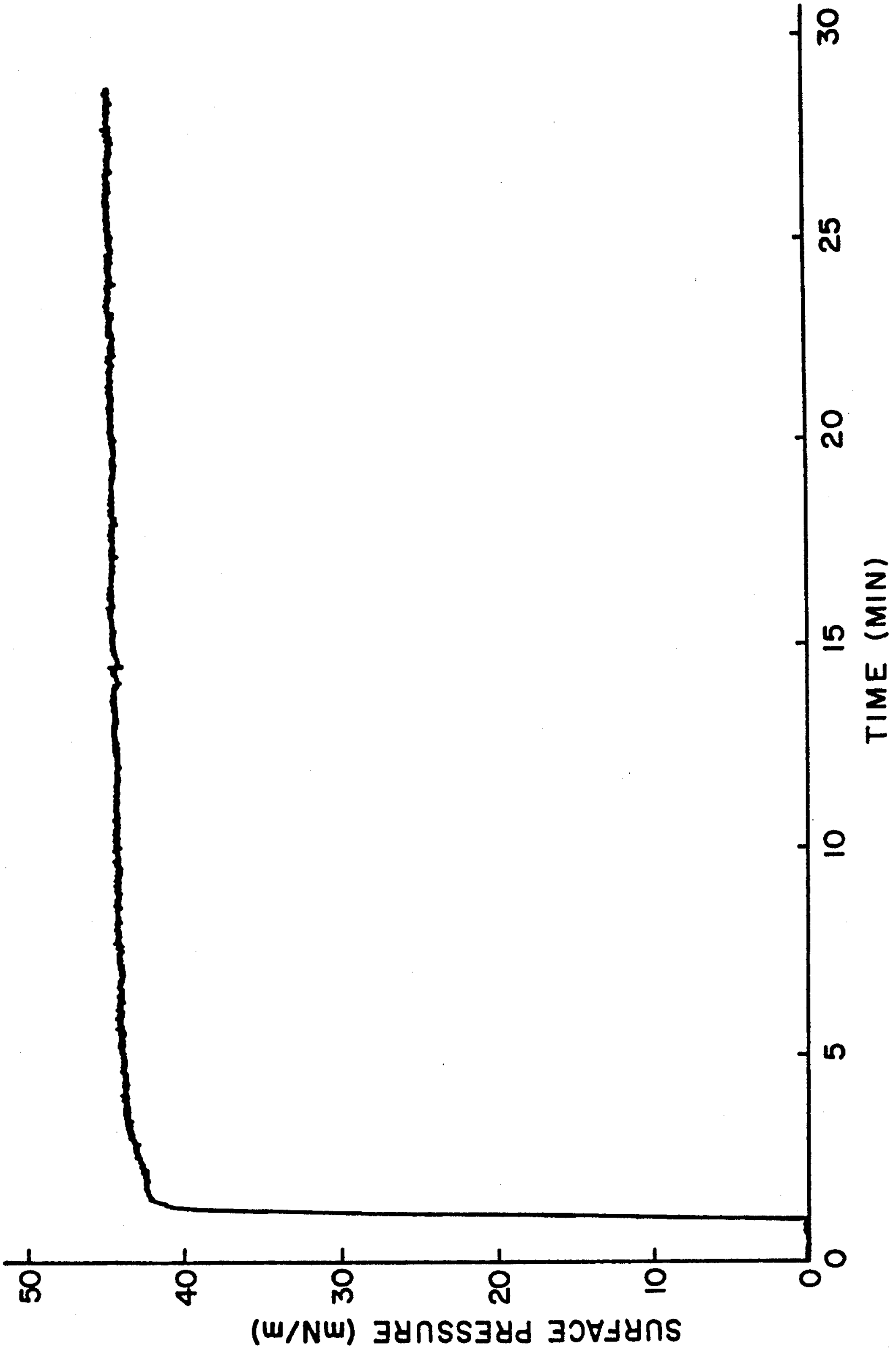
Figure 15:
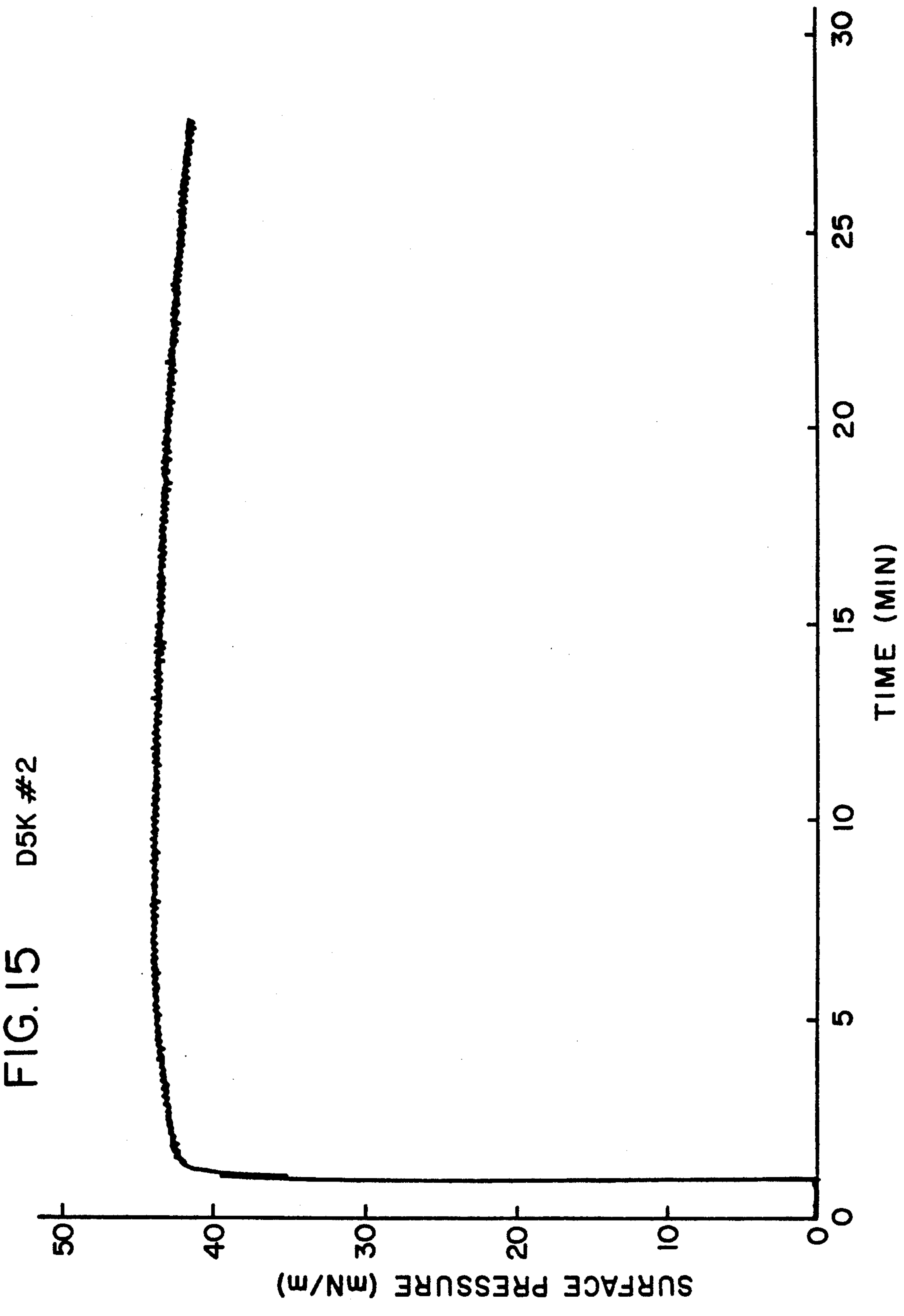

The SP-5-derived synthetic peptide, hSP-5(30-59), has reduced activity (FIG. 13). That this loss of activity is not specifically due to the absence of the cysteine residues at positions 28 and 29 is suggested by the observation that the D5K#1 synthetic peptide ($S^{28}$, $S^{29}$-hSP-5(24-59)), in which these cysteine residues were replaced with serines, showed full activity (FIG. 15). This result implies that the reduction in polypeptide length, rather than loss of specific residues, results in the loss of ASP activity.

The D5K#1 peptide ($S^{28}$,$S^{29}$-hSP-5(24-59)) was produced recombinantly and purified as described in Example 2. The recombinant SP-5 peptide ($S^{28}$, $S^{29}$-hSP-5(24-59)) was tested using the standard protocol for in vitro assay with the following modification: the phospholipid formulation was 7 parts DPPC: 3 parts POPG where POPG is (palmitoyl-oleoyl PG). The final formulation was 20 parts phospholipid mixture: 1 part protein by weight. The Ser-Ser analog was highly active in vitro and at least as effective as purified rabbit surfactant in vivo.

The D5K#1 synthetic peptide ($S^{28}$, $S^{29}$-hSP-5(24-59)) peptide analog was also active in vivo when tested according to the procedure set forth in W087/06588, as shown below:

| D5K#1 $S^{28}S^{29}$-hSP-5(24-59) (cys → ser change | | |
|---|---|---|
| | $P_{ins}$ at 30 minutes: | |
| n = 4 | cys → ser | 18.0 ± 0.7 (SD) cm of $H_2O$ |
| | rabbit surfactant | 18.5 ± 1.2 cm of $H_2O$ |
| | NaCl | 34.6 ± 1.2 cm of $H_2O$ |
| | $C_{TOT}$ at 30 minutes: | |
| | cys → ser peptide | 0.486 ± 0.3 |
| | rabbit surfactant | 0.494 ± 0.7 |
| | NaCl | 0.224 ± 0.2 |

Recombinant $S^{28}$, $S^{29}$-hSP-5(24-59) has also been tested in vivo and is at least as effective as purified rabbit surfactant.

Figure 17:
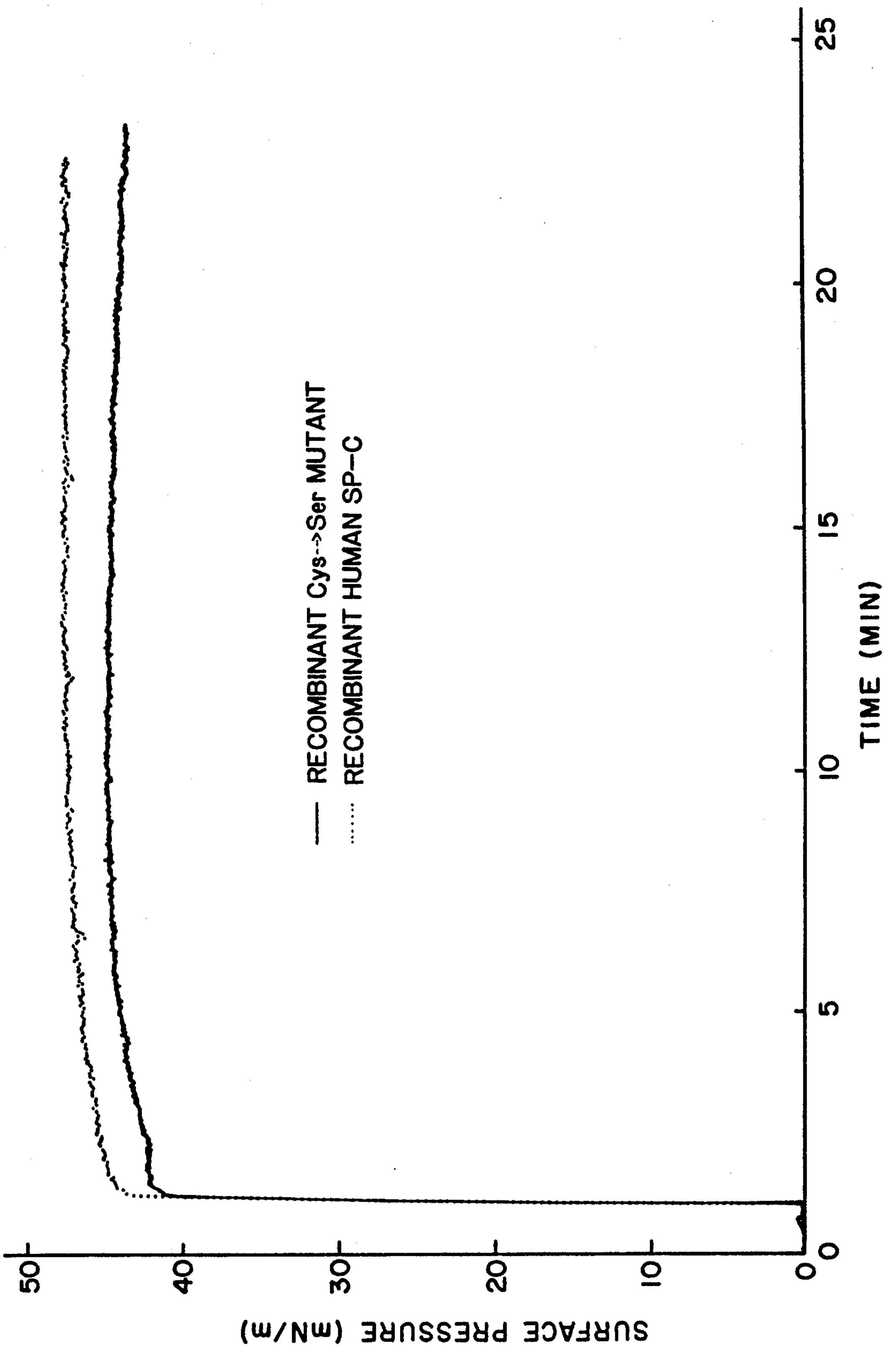
Figure 18:
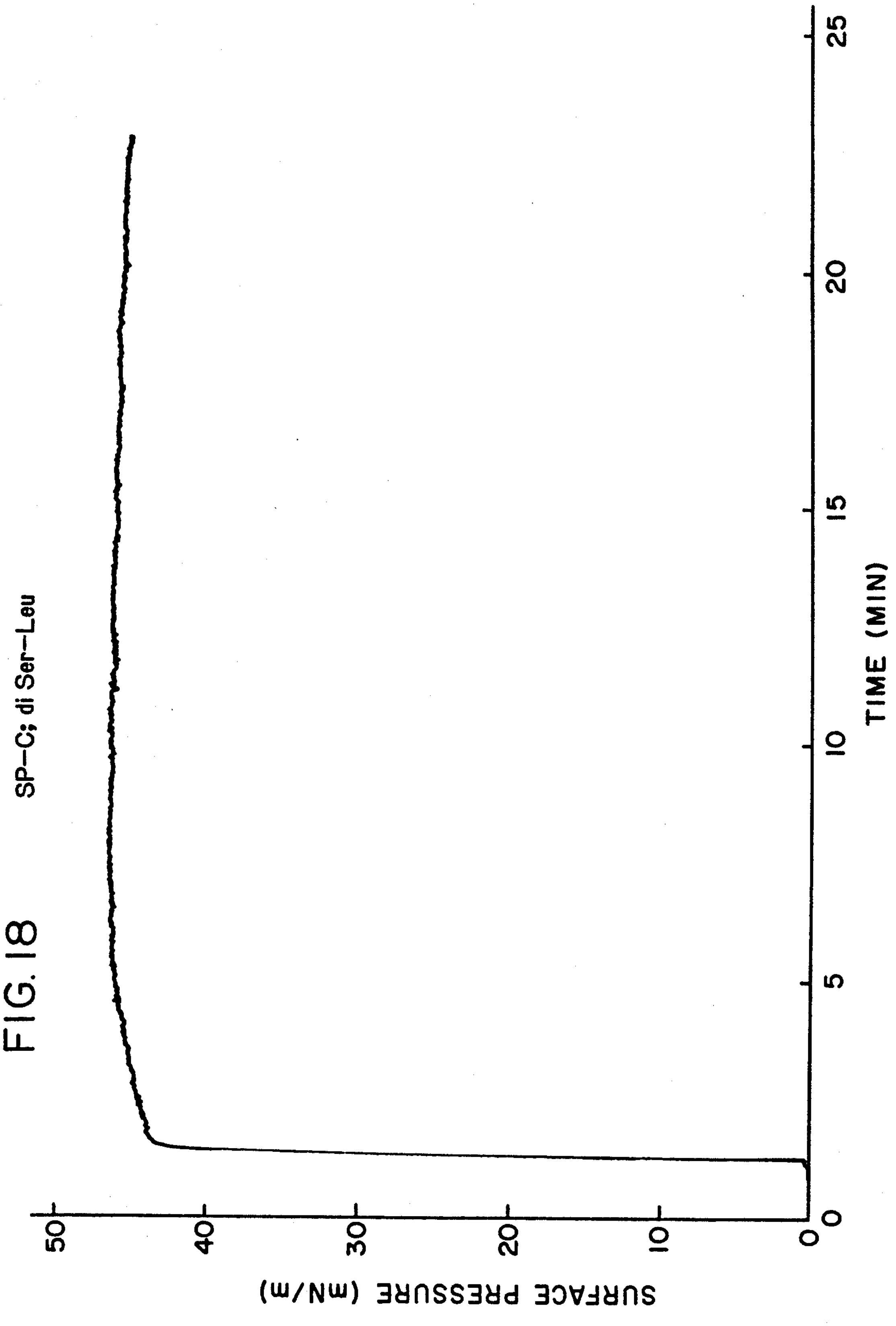

The peptide $S^{28}$, $S^{29}$-hSP-5(25-59) was produced recombinantly in bacteria as described in Example 3 and purified. Using standard techniques of site-directed mutagenesis, the vector for this peptide was modified to eliminate the codon for His(59). The vector was used to recombinantly produce the peptide $S^{28}$, $S^{29}$-hSP-5(24-58). The recombinant peptide $S^{28}$, $S^{29}$-hSP-5(24-59) and hSP-5(24-59) i.e., the peptide without the Ser-Ser mutation, were tested side-by-side using the standard protocol for the in vitro assay with the following modification: the phospholipid formulation was 7 parts DPPC: 3 parts POPG. The final formulation was 20 parts phospholipid mixture: 1 part protein by weight. The superimposed plots of surface pressure, shown in FIG. 17, indicate that the Ser-Ser analog was at least as effective in vitro as the corresponding recombinant protein having the native The $S^{28}$, $S^{29}$-hSP-5(24-59) peptide was also tested in the in vitro assay with the same modifications. The plot of surface pressure, presented in FIG. 18, indicates that removal of His(59) does not change the efficacy of the protein.

The recombinantly produced peptides $S^{28}$, $S^{29}$-hSP-5(24-59), $S^{28}$, $S^{29}$-hSP-5(25-58) and hSP(25-59) were tested in vivo and compared with isolated rabbit surfactant. Results are shown below:

| $P_{ins}$ at 30 minutes: | |
|---|---|
| rabbit surfactant | 17.5 cm of $H_2O$ |
| $S^{28}$,$S^{29}$-hSP-5(24-59) | 16.0 cm of $H_2O$ |
| $S^{28}$,$S^{29}$-hSP-5(25-58) | 16.0 cm of $H_2O$ |
| hSP(25-59) | 16.0 cm of $H_2O$ |

Figure 16:
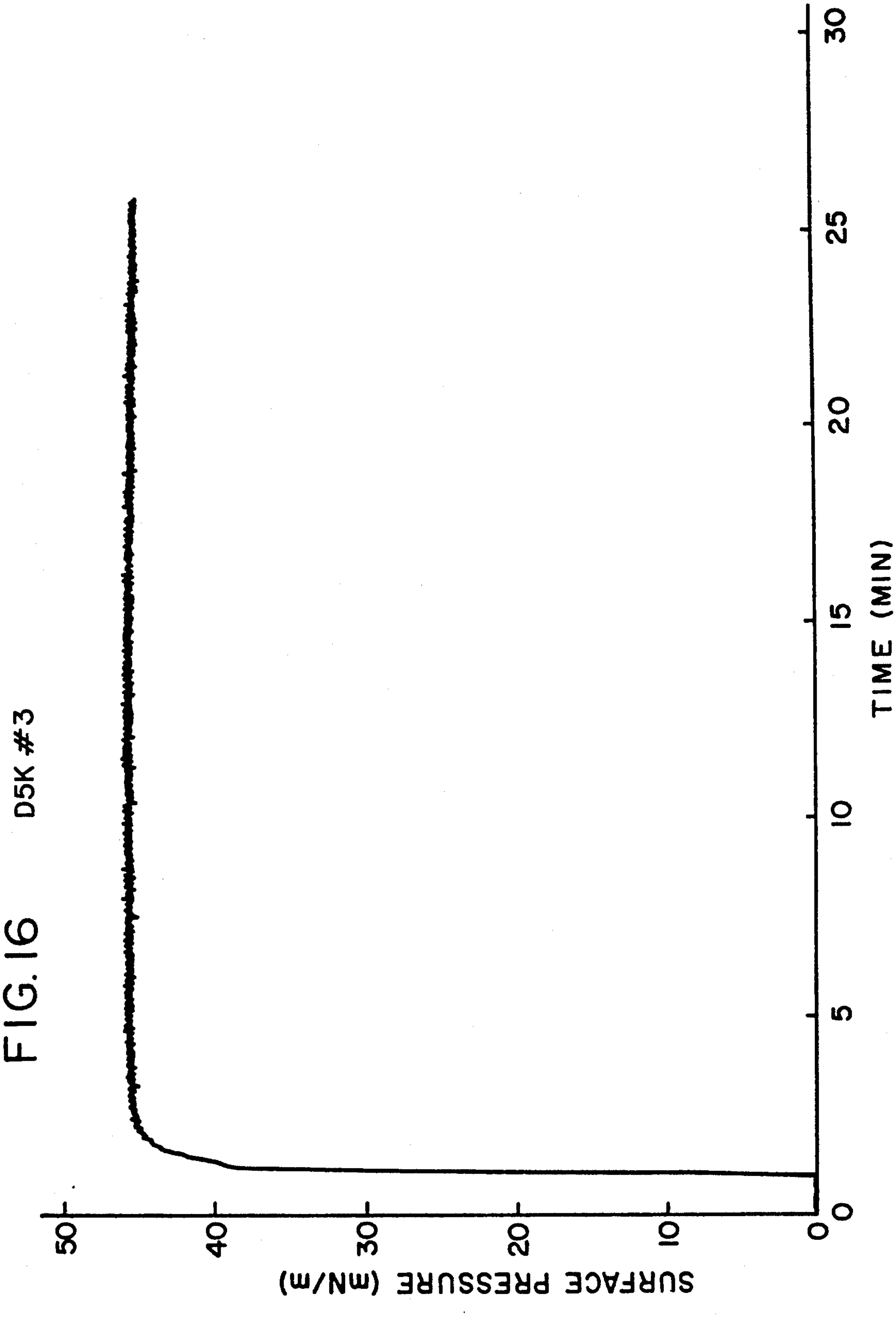

Further suggestion that specific amino terminal sequences are not a requirement for full activity is provided by the analysis of D5K#2 and D5K#3. These peptides, in which more extensive substitutions have been made in the amino terminal region, also retain full activity in vitro (FIGS. 15 and 16).

Other peptides which the inventors herein believe may be useful in the present method are the 31-61, 30-61, 28-61 and 26-61 peptides of the human SP-5-encoded protein shown in FIG. 3.

We claim:

1. A recombinant expression system capable, when transformed into a recombinant host, of expressing a DNA encoding a polypeptide having ASP activity and defined by the sequence X—$AA_{28}$—$AA_{29}$—$AA_{30}$—$AA_{31}$—$AA_{32}$—$AA_{33}$—$AA_{34}$—$AA_{35}$—

Leu—Leu—Ile—Z—Z—Z—Z—Z—Z—Leu—Ile—Z—Z—Z—

-continued

Ile—Z—Gly—Ala—Leu—Leu—Met—Y, wherein:

$AA_{28}$ is Ser,
$AA_{29}$ is Ser,
$AA_{30}$ is Pro or Ala,
$AA_{31}$ is Val or Gln,
$AA_{32}$ is His or Lys,
$AA_{33}$ is Leu or Ala,
$AA_{34}$ is Lys or Gln,
$AA_{35}$ is Arg or Gln,
Z is either Val or Ile,
Y is OH, Gly-OH, Gly-Leu-OH, Gly-Leu-His-OH, or Gly-Leu-His-$Y_1$, wherein $Y_1$ is a C-terminal extension sequence of 1-15 amino acids corresponding to amino acids 60-74 in FIG. 3, and
X is H or an amino acid sequence selected from the group consisting of H-$AA_{27}$-, H-$AA_{26}$-$AA_{27}$, or X'-$AA_{26}$-$AA_{27}$,
wherein:
$AA_{27}$ is Pro or Ala,
$AA_{26}$ is Ile or Ser, and
X' is H or an N-terminal extension sequence of 1-25 amino acids corresponding to amino acids 1-25 in FIG. 3, wherein said expression system comprises said encoding DNA operably linked to control sequences which effect its expression.

2. A recombinant host transformed with the expression system of claim 1.

3. A method to produce a polypeptide having ASP activity and defined by the sequence X—$AA_{28}$—$AA_{29}$—$AA_{30}$—$AA_{31}$—$AA_{32}$—$AA_{33}$—$AA_{34}$—$AA_{35}$—

Leu—Leu—Ile—Z—Z—Z—Z—Z—Z—Leu—Ile—Z—Z—Z—

Ile—Z—Gly—Ala—Leu—Leu—Met—Y, wherein:

$AA_{28}$ is Ser,
$AA_{29}$ is Ser,
$AA_{30}$ is Pro or Ala,
$AA_{31}$ is Val or Gln,
$AA_{32}$ is His or Lys,
$AA_{33}$ is Leu or Ala,
$AA_{34}$ is Lys or Gln,
$AA_{35}$ is Arg or Gln,
Z is either Val or Ile,
Y is OH, Gly-OH, Gly-Leu-OH, Gly-Leu-His-OH, or Gly-Leu-His-$Y_1$, wherein $Y_1$ is a C-terminal extension sequence of 1-15 amino acids corresponding to amino acids 60-74 in FIG. 3, and
X is H or an amino acid sequence selected from the group consisting of H-$AA_{27}$-, H-$AA_{26}$-$AA_{27}$, or X'-$AA_{26}$-$AA_{27}$,
wherein:
$AA_{27}$ is Pro or Ala,
$AA_{26}$ is Ile or Ser, and
X' is H or an N-terminal extension sequence of 1-25 amino acids corresponding to amino acids 1-25 in FIG. 3, which method comprises culturing the recombinant host of claim 2 under conditions which permit expression of said coding DNA to produce said polypeptide, and recovering the polypeptide from the culture.

4. A recombinant DNA in isolated form consisting essentially of DNA encoding a polypeptide having ASP activity and defined by the sequence X—$AA_{28}$—$AA_{29}$—$AA_{30}$—$AA_{31}$—$AA_{32}$—$AA_{33}$—$AA_{34}$—$AA_{35}$—Leu—Leu—Ile—Z—Z—Z—Z—Z—Z—Leu—Ile—Z—Z—Z—Ile—Z—Gly—Ala—Leu—Leu—Met—Y, wherein:

$AA_{28}$ is Ser,
$AA_{29}$ is Ser,
$AA_{30}$ is Pro or Ala,
$AA_{31}$ is Val or Gln,
$AA_{32}$ is His or Lys,
$AA_{33}$ is Leu or Ala,
$AA_{34}$ is Lys or Gln,
$AA_{35}$ is Arg or Gln,
Z is either Val or Ile,
Y is OH, Gly-OH, Gly-Leu-OH, Gly-Leu-His-OH, or Gly-Leu-His-$Y_1$, wherein $Y_1$ is a C-terminal extension sequence of 1-15 amino acids corresponding to amino acids 60-74 in FIG. 3, and
X is H or an amino acid sequence selected from the group consisting of H-$AA_{27}$-, H-$AA_{26}$-$AA_{27}$, or X'-$AA_{26}$-$AA_{27}$,
wherein:
$AA_{27}$ is Pro or Ala,
$AA_{26}$ is Ile or Ser, and
X' is H or an N-terminal extension sequence of 1-25 amino acids corresponding to amino acids 1-25 in FIG. 3.

* * * * *